United States Patent [19]

Flanigen et al.

[11] Patent Number: 4,940,570
[45] Date of Patent: * Jul. 10, 1990

[54] BERYLLIUM-ALUMINUM-PHOSPHORUS-OXIDE MOLECULAR SIEVE COMPOSITIONS

[75] Inventors: Edith M. Flanigen, White Plains; Brent M. Lok, New City; Robert L. Patton, Katonah; Stephen T. Wilson, Shrub Oak, all of N.Y.

[73] Assignee: UOP, Des Plaines, Ill.

[ * ] Notice: The portion of the term of this patent subsequent to Aug. 11, 2004 has been disclaimed.

[21] Appl. No.: 835,293

[22] Filed: Mar. 3, 1986

Related U.S. Application Data

[63] Continuation-in-part of Ser. No. 599,776, Apr. 13, 1984, abandoned.

[51] Int. Cl.$^5$ ............................................. C01B 25/36
[52] U.S. Cl. .................................................... 423/306
[58] Field of Search ................ 423/305, 306; 502/208, 502/214

[56] References Cited

U.S. PATENT DOCUMENTS

| | | | |
|---|---|---|---|
| 3,911,088 | 10/1975 | Marosi et al. | 423/328 M |
| 3,941,871 | 3/1976 | Dwyer et al. | 423/326 |
| 3,996,337 | 12/1976 | Stabellow et al. | 423/328 M |
| 4,061,724 | 12/1977 | Grose et al. | 423/335 |
| 4,126,665 | 11/1978 | Ropp | 423/305 |
| 4,310,440 | 1/1982 | Wilson et al. | 252/435 |
| 4,420,467 | 12/1983 | Whittam | 423/328 |
| 4,440,871 | 4/1984 | Lok et al. | 502/214 |
| 4,456,582 | 6/1984 | Marosi et al. | 423/326 |
| 4,500,651 | 2/1985 | Lok et al. | 502/208 |
| 4,554,143 | 11/1985 | Messina et al. | 423/306 |
| 4,567,029 | 1/1986 | Wilson et al. | 423/306 |

FOREIGN PATENT DOCUMENTS

| | | |
|---|---|---|
| 0054364 | 6/1982 | European Pat. Off. . |
| 0055046 | 6/1982 | European Pat. Off. . |
| 0055529 | 7/1982 | European Pat. Off. . |
| 0059059 | 9/1982 | European Pat. Off. . |
| 2334920 | 4/1975 | Fed. Rep. of Germany ... 423/328 M |
| 2353921 | 5/1975 | Fed. Rep. of Germany ... 423/328 M |
| 0099199 | 6/1983 | Japan ............................. 423/328 M |
| 0115092 | 7/1983 | Japan ............................. 423/328 M |
| 874615 | 10/1981 | U.S.S.R. ............................... 423/306 |
| 2078704 | 1/1982 | United Kingdom ................ 423/326 |

OTHER PUBLICATIONS

Haggin "Chemical & Engineering" Jun. 20, 1983, pp. 36 and 37.

Primary Examiner—John Doll
Assistant Examiner—R. Bruce Breneman
Attorney, Agent, or Firm—Thomas K. McBride; Eugene I. Snyder; Frank S. Molinaro

[57] ABSTRACT

Molecular sieve compositions having three-dimensional microporous framework structures of $BeO_2$, $AlO_2$ and $PO_2$ tetrahedral oxide units are disclosed. These molecular sieves have an empirical chemical composition on an anhydrous basis expressed by the formula:

$$mR:(Be_xAl_yP_z)O_2$$

wherein "R" represents at least one organic templating agent present in the intracrystalline pore system; "m" represents the molar amount of "R" present per mole of $(Be_xAl_yP_z)O_2$; and "x", "y" and "z" represent the mole fractions of beryllium, aluminum and phosphorus, respectively, present as tetrahedral oxides. Their use as adsorbents, catalysts, etc. is also disclosed.

60 Claims, 3 Drawing Sheets

BERYLLIUM-ALUMINUM-PHOSPHORUS-OXIDE MOLECULAR SIEVE COMPOSITIONS

This application is a continuation-in-part of our co-pending application Ser. No. 599,776 filed Apr. 13, 1984, now abandoned.

FIELD OF THE INVENTION

The instant invention relates to a novel class of crystalline microporous molecular sieves and to the method of their preparation. The invention relates to novel beryllium-aluminum-phosphorus-oxide molecular sieves containing framework tetrahedral oxide units of beryllium, aluminum and phosphorus. These compositions may be prepared hydrothermally from gels containing reactive compounds of beryllium, aluminum and phosphorus capable of forming framework tetrahedral oxides, and preferably at least one organic templating agent which functions in part to determine the course of the crystallization mechanism and the structure of the crystalline product.

BACKGROUND OF THE INVENTION

Molecular sieves of the crystalline alumino-silicate zeolite type are well known in the art and now comprise over 150 species of both naturally occurring and synthetic compositions. In general the crystalline zeolites are formed from corner-sharing $AlO_2$ and $SiO_2$ tetrahedra and are characterized by having pore openings of uniform dimensions, having a significant ion-exchange capacity and being capable of reversibly desorbing an adsorbed phase which is dispersed throughout the internal voids of the crystal without displacing any atoms which make up the permanent crystal structure.

Other crystalline microporous compositions which are not zeolitic, i.e. do not contain $AlO_2$ tetrahedra as essential framework constituents, but which exhibit the ion-exchange and/or adsorption characteristics of the zeolites are also known. Metal organosilicates which are said to possess ion-exchange properties, have uniform pores and are capable of reversibly adsorbing molecules having molecular diameters of about 6 Å or less, are reported in U.S. Pat. No. 3,941,871 issued Mar. 2, 1976 to Dwyer et al. A pure silica polymorph, silicalite, having molecular sieving properties and a neutral framework containing neither cations nor cation sites is disclosed in U.S. Pat. No. 4,061,724 issued Dec. 6, 1977 to R. W. Grose et al.

A recently reported class of microporous compositions and the first framework oxide molecular sieves synthesized without silica, are the crystalline aluminophosphate compositions disclosed in U.S. Pat. No. 4,310,440 issued Jan. 12, 1982 to Wilson et al. These materials are formed from $AlO_2$ and $PO_2$ tetrahedra and have electrovalently neutral frameworks as in the case of silica polymorphs. Unlike the silica molecular sieve, silicalite, which is hydrophobic due to the absence of extra-structural cations, the aluminophosphate molecular sieves are moderately hydrophilic, apparently due to the difference in electronegativity between aluminum and phosphorus. Their intracrystalline pore volumes and pore diameters are comparable to those known for zeolites and silica molecular sieves.

In U.S. Pat. Nc. 4,440,871 there is described a novel class of silicon-substituted aluminophosphates which are both microporous and crystalline. The materials have a three dimensional crystal framework of $PO_2^+$, $AlO_2^-$ and $SiO_2$ tetrahedral units and, exclusive of any alkali metal or calcium which may optionally be present, an as-synthesized empirical chemical composition on an anhydrous basis of:

$$mR:(Si_xAl_yP_z) O_2$$

wherein "R" represents at least one organic templating agent present in the intracrystalline pore system; "m" represents the moles of "R" present per mole of $(Si_xAl_yP_z)O_2$ and has a value of from zero to 0.3, the maximum value in each case depending upon the molecular dimensions of the templating agent and the available void volume of the pore system of the particular silicoaluminophosphate species involved; and "x", "y", and "z" represent the mole fractions of silicon, aluminum and phosphorus, respectively, present as tetrahedral oxides. The minimum value for each of "x", "y", and "z" is 0.01 and preferably 0.02. The maximum value for "x" is 0.98; for "y" is 0.60; and for "z" is 0.52. These silicoaluminophosphates exhibit several physical and chemical properties which are characteristic of aluminosilicate zeolites and aluminophosphates.

In U.S. Pat. No. 4,500,651, there is described a novel class of titanium-containing molecular sieves whose chemical composition in the as-synthesized and anhydrous form is represented by the unit empirical formula:

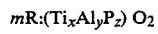

$$mR:(Ti_xAl_yP_z) O_2$$

wherein "R" represents at least one organic templating agent present in the intracrystalline pore system; "m" represents the moles of "R" present per mole of $(Ti_xAl_yP_z)O_2$ and has a value of between zero and about 5.0; and "x", "y" and "z" represent the mole fractions of titanium, aluminum and phosphorus, respectively, present as tetrahedral oxides.

In U.S. Pat. No. 4,567,029, there is described a novel class of crystalline metal aluminophosphates having three-dimensional microporous framework structures of $MO_2$, $AlO_2$ and $PO_2$ tetrahedral units and having an empirical chemical composition on an anhydrous basis expressed by the formula:

$$mR:(M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3; "M" represents at least one metal of the group magnesium, manganese, zinc and cobalt; "x", "y", and "z" represent the mole fractions of the metal "M", aluminum and phosphorus, respectively, present as tetrahedral oxides.

In U.S. Pat. No. 4,544,143, there is described a novel class of crystalline ferroaluminophosphates having a three-dimensional microporous framework structure of $FeO_2$, $AlO_2$ and $PO_2$ tetrahedral units and having an empirical chemical composition on an anhydrous basis expressed by the formula:

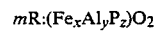

$$mR:(Fe_xAl_yP_z)O_2$$

wherein "R" represents at least one organic templating agent present in the intracrystalline pore system; "m" represents the moles of "R" present per mole of $(Fe_xAl_yP_z)O_2$ and has a value of from zero to 0.3; and "x", "y" and "z" represent the mole fractions of the iron, aluminum and phosphorus, respectively, present as tetrahedral oxides.

The instant invention relates to new molecular sieve compositions having framework tetrahedral units of $BeO_2^{-2}$, $AlO_2^-$ and $PO_2^+$.

SUMMARY OF THE INVENTION

Figure 1:
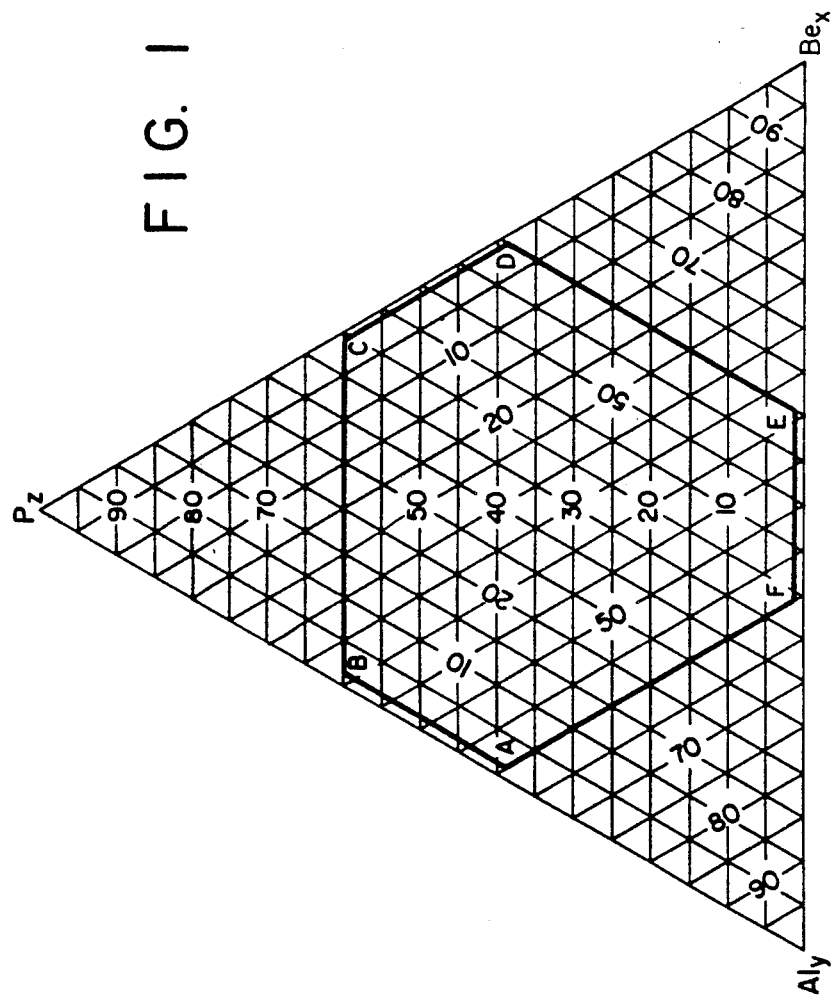
FIG. 1 is a ternary diagram wherein parameters relating to the instant compositions are set forth as mole fractions.

The instant invention relates to a new class of beryllium-aluminum-phosphorus-oxide molecular sieves having a crystal framework structure of $BeO_2^{-2}$, $AlO_2^-$ and $PO_2^+$ tetrahedral oxide units. These new molecular sieves exhibit ion-exchange, adsorption and catalytic properties and, accordingly, find wide use as adsorbents and catalysts. The members of this novel class of compositions have crystal framework structures of $BeO_2^{-2}$, $AlO_2^-$ and $PO_2^+$ tetrahedral units and have an empirical chemical composition on an anhydrous basis expressed by the formula:

$$mR:(Be_xAl_yP_z)O_2$$

wherein "R" represents at least one organic templating agent present in the intracrystalline pore system; "m" represents the molar amount of "R" present per mole of $(Be_xAl_yP_z)O_2$ and has a value of zero to about 0.3; and "x", "y" and "z" represent the mole fractions of beryllium, aluminum and phosphorus, respectively, present as tetrahedral oxides. These molecular sieve compositions comprise crystalline molecular sieves having a three-dimensional microporous framework structure of $BeO_2^{-2}$, $AlO_2^-$ and $PO_2^+$ tetrahedral units.

The molecular sieves of the instant invention will be generally referred to by the acronym "BeAPO" to designate the framework of $BeO_2^{-2}$, $AlO_2^-$ and $PO_2^+$ tetrahedral units. Actual class members will be identified by denominating the various structural species which make up the BeAPO class by assigning a number and, accordingly, are identified as "BeAPO-i" wherein "i" is an integer. The given species designation is not intended to denote a similarity in structure to any other species denominated by a numbering system.

DETAILED DESCRIPTION OF THE INVENTION

The instant invention relates to a new class of beryllium-aluminum-phosphorus-oxide molecular sieves comprising a crystal framework structure of $BeO_2^{-2}$, $AlO_2^-$ and $PO_2^+$ tetrahedral oxide units. These new molecular sieves exhibit ion-exchange, adsorption and catalytic properties and, accordingly, find wide use as adsorbents and catalysts.

The BeAPO molecular sieves have three-dimensional microporous framework structures of $BeO_2^{-2}$, $AlO_2^-$, and $PO_2^+$ tetrahedral oxide units having an empirical chemical composition on an anhydrous basis expressed by the formula:

$$mR:(Be_xAl_yP_z)O_2$$

wherein "R" represents at least one organic templating agent present in the intracrystalline pore system; "m" represents the molar amount of "R" present per mole of $(Be_xAl_yP_z)O_2$ a value of zero to about 0.3 but is preferably not greater than about 0.15; and "x", "y" and "z" represent the mole fractions of beryllium, aluminum and phosphorus, respectively, present as tetrahedral oxides. The mole fractions "x", "y", and "z" are generally defined as being within the hexagonal compositional area defined by points A, B, C, D, E and F of the ternary diagram of FIG. 1. Points A, B, C, D, E and F of FIG. 1 have the following values for "x", "y", and "z":

| Point | Mole Fraction | | |
|---|---|---|---|
| | x | y | z |
| A | 0.01 | 0.60 | 0.39 |
| B | 0.01 | 0.39 | 0.60 |
| C | 0.39 | 0.01 | 0.60 |
| D | 0.60 | 0.01 | 0.39 |
| E | 0.60 | 0.39 | 0.01 |
| F | 0.39 | 0.60 | 0.01 |

Figure 2:
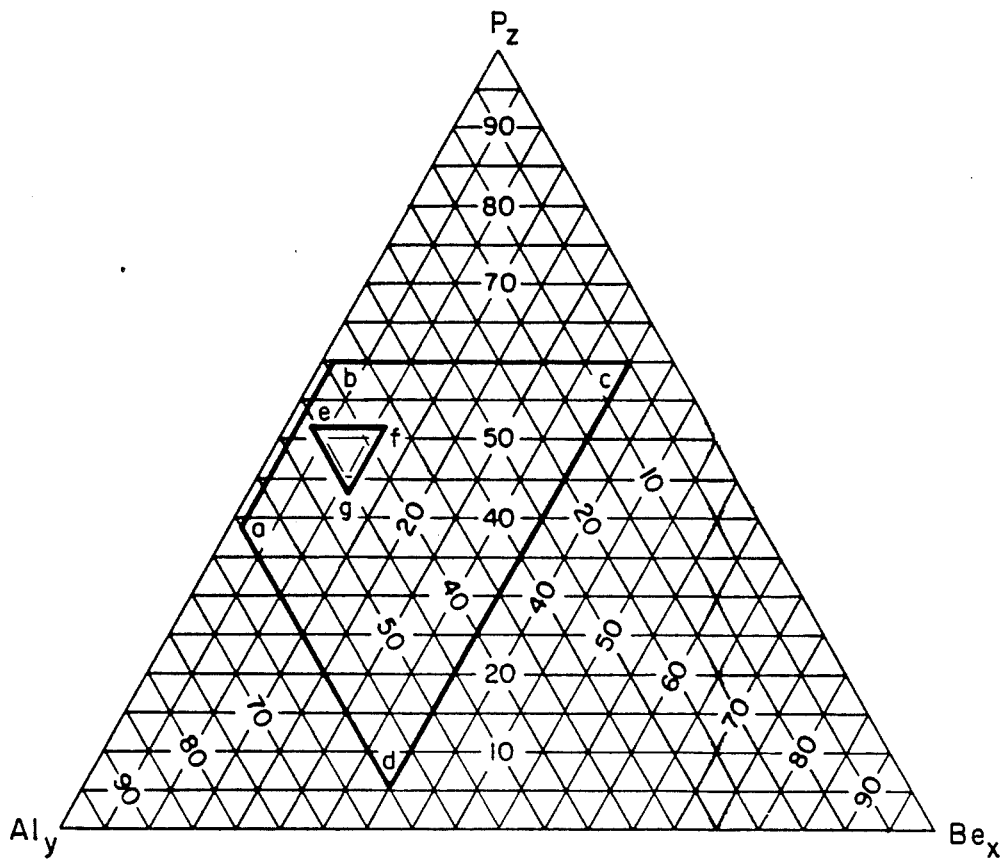
FIG. 2 is a ternary diagram wherein parameters relating to preferred compositions are set forth as mole fractions.

In a preferred subclass of the BeAPO molecular sieves the values of "x", "y" and "z" in the above formula are within the tetragonal compositional area defined by the points a, b, c and d of the ternary diagram which is FIG. 2 of the drawings, said points a, b, c and d representing the following values for "x", "y" and "z":

| Point | Mole Fraction | | |
|---|---|---|---|
| | x | y | z |
| a | 0.01 | 0.60 | 0.39 |
| b | 0.01 | 0.39 | 0.60 |
| c | 0.35 | 0.05 | 0.60 |
| d | 0.35 | 0.60 | 0.05 |

In an especially preferred subclass of the BeAPO molecular sieves the values of "x", "y" and "z" in the formula are within the triangular compositional area defined by the points e, f and g of the ternary diagram which is FIG. 2 of the drawings, said points e, f and g representing the following values for "x", "y" and "z":

| Point | Mole Fraction | | |
|---|---|---|---|
| | x | y | z |
| e | 0.02 | 0.46 | 0.52 |
| f | 0.10 | 0.38 | 0.52 |
| g | 0.10 | 0.46 | 0.44 |

The BeAPOs of this invention are useful as adsorbents, catalysts, ion-exchangers, and the like in much the same fashion as aluminosilicates have been employed heretofore, although their chemical and physical properties are not necessarily similar to those observed for aluminosilicates.

BeAPO compositions are generally synthesized by hydrothermal crystallization from a reaction mixture containing reactive sources of beryllium, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure, at a temperature between 50° and 250° C., and preferably between 100° C. and 200° C., until crystals of the BeAPO product are obtained, usually a period of from several hours to several weeks. Typical crystallization times are from about 2 hours to about 30 days with from about 4 hours to about 14 days, and preferably about 1 to about 7 days, being generally employed to obtain crystals of the BeAPO products The product is recovered by any convenient method such as centrifugation or filtration.

In synthesizing the BeAPO compositions of the instant invention, it is preferred to employ a reaction mixture composition expressed in terms of the molar ratios as follows:

$$aR:(Be_uAl_vP_w)O_2 \cdot bH_2O$$

wherein "R" is an organic templating agent; "a" is the amount of organic templating agent "R" and has a value of from zero to about 6 and is preferably an effective amount within the range of greater than zero (0) to about 6 and most preferably not more than about 1.5; "b" has a value of from zero (0) to about 500, preferably between about 2 and about 300, most preferably not more than about 50; and "u", "v" and "w" represent the mole fractions of beryllium, aluminum and phosphorus, respectively, and each has a value of at least 0.01. The mole fractions "u", "v" and "w" in the reaction mixture are preferably within the pentagonal compositional area defined by points G, H, I, J and K which is shown in FIG. 3 of the drawings, where points G, H, I, J and K have the following values for "u", "v" and "w":

| Point | Mole Fraction | | |
|---|---|---|---|
| | u | v | w |
| G | 0.01 | 0.60 | 0.39 |
| H | 0.01 | 0.39 | 0.60 |
| I | 0.39 | 0.01 | 0.60 |
| J | 0.98 | 0.01 | 0.01 |
| K | 0.39 | 0.60 | 0.01 |

Figure 3:
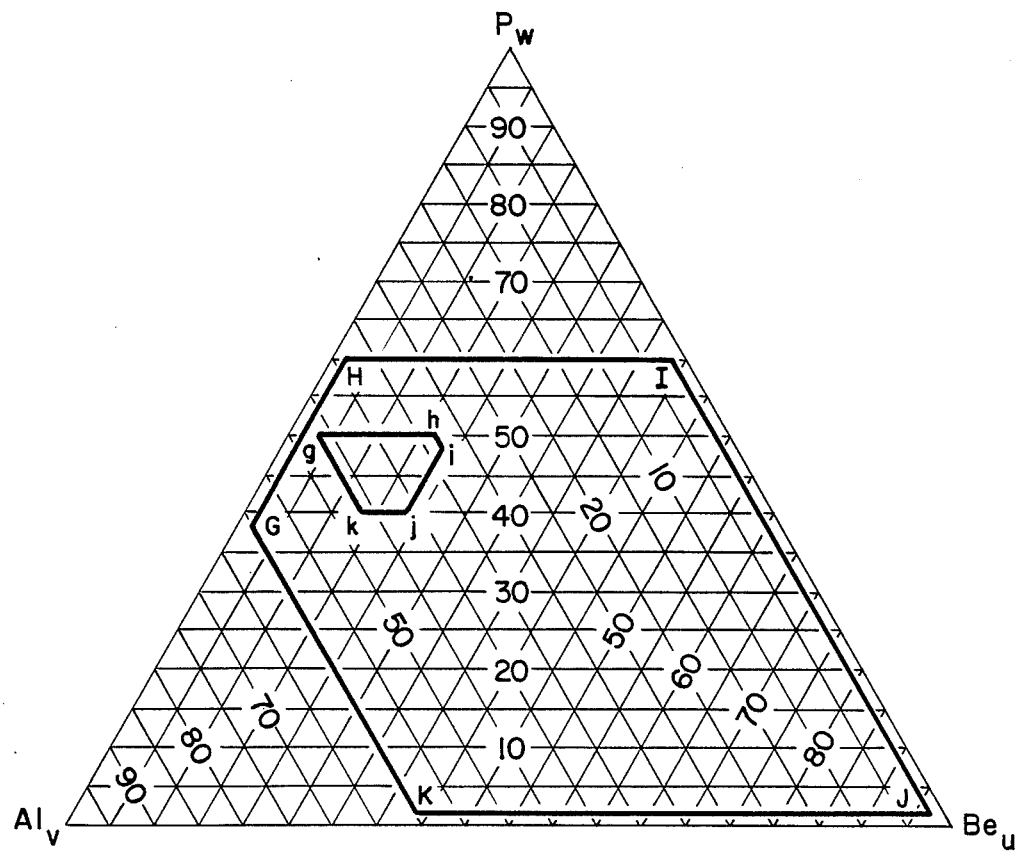
FIG. 3 is a ternary diagram wherein parameters relating to the reaction mixtures employed in the preparation of the compositions of this invention are set forth as mole fractions.

Especially preferred reaction mixture compositions are those within the pentagonal compositional area defined by points g, h, i, j and k which is shown in FIG. 3 of the drawings, where points g, h, i j and k have the following values for "u", "v" and "w":

| Point | Mole Fraction | | |
|---|---|---|---|
| | x | y | z |
| g | 0.04 | 0.46 | 0.50 |
| h | 0.16 | 0.34 | 0.50 |
| i | 0.17 | 0.34 | 0.49 |
| j | 0.17 | 0.43 | 0.40 |
| k | 0.14 | 0.46 | 0.40 |

In the foregoing expression of the reaction composition, the reactants are normalized with respect to the total of $u+v+w=1.00$ mole, whereas in the examples the reaction mixtures are expressed in terms of the molar oxide ratios and may be normalized to 1.00 mole of $P_2O_5$. This latter form is readily converted to the former form by routine calculation by dividing the total number of moles of beryllium, aluminum and phosphorus into the moles of each of beryllium, aluminum and phosphorus. The moles of template and water are similarly normalized.

In forming the reaction mixture from which the instant molecular sieves are formed the organic templating agent can be any of these heretofore proposed for use in the synthesis of conventional zeolite aluminosilicates. In general these compounds contain elements of Group VA of the Periodic Table of Elements, particularly nitrogen, phosphorus, arsenic and antimony, preferably nitrogen or phosphorus and most preferably nitrogen, which compounds also contain at least one alkyl or aryl group having from 1 to 8 carbon atoms. Particularly preferred compounds for use as templating agents are the amines, quaternary phosphonium and quaternary ammonium compounds, the latter being represented generally by the formula $R_4X^+$ wherein "X" is nitrogen or phosphorus and each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. The mono-, di- and tri-amines are advantageously utilized, either alone or in combination with a quaternary ammonium compound or other templating compound. Mixtures of two or more templating agents can either produce mixtures of the desired BeAPOs or the more strongly directing templating species may control the course of the reaction with the other templating species serving primarily to establish the pH conditions of the reaction gel. Representative templating agents include tetramethylammonium, tetraethylammonium, tetrapropylammonium or tetrabutylammonium ions; tetrapentylammonium ion; di-n-propylamine; tripropylamine; triethylamine; triethanolamine; piperidine; cyclohexylamine; 2-methylpyridine; N,N-dimethylbenzylamine; N,N-dimethylethanolamine; choline; N,N'-dimethylpiperazine; 1,4-diazabicyclo (2,2,2,) octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; di-n-butylamine; neopentylamine; di-n-pentylamine; isopropylamine; t-butylamine; ethylenediamine; pyrrolidine; and 2-imidazolidone. Not every templating agent will direct the formation of every species of BeAPO, i.e., a single templating agent can, with proper manipulation of the reaction condition, direct the formation of several BeAPO compositions, and a given BeAPO composition can be produced using several different templating agents.

The reactive phosphorus source is preferably phosphoric acid, but organic phosphates such as triethyl phosphate may be satisfactory, and so also may crystalline or amorphous aluminophosphates such as the $AlPO_4$ composition of U.S. Pat. No. 4,310,440. Organophosphorus compounds, such as tetrabutylphosphonium bromide, do not apparently serve as reactive sources of phosphorus, but these compounds may function as templating agents. Conventional phosphorus salts such as sodium metaphosphate, may be used, at least in part, as the phosphorus source, but are not preferred.

The preferred aluminum source is either an aluminum alkoxide, such as aluminum isoproproxide, or pseudo-boehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The reactive source of beryllium can be introduced into the reaction system in any form which permits the formation in situ of a reactive form of beryllium, i.e., reactive to form the framework tetrahedral oxide unit of beryllium. Compounds of beryllium which may be employed include oxides, alkoxides, hydroxides, chlorides, bromides, iodides, nitrates, sulfates, carboxylates (e.g., acetates) and the like.

While not essential to the synthesis of BeAPO compositions, stirring or other moderate agitation of the reaction mixture and/or seeding the reaction mixture with seed crystals of either the BeAPO species to be produced or a topologically similar aluminophosphate, aluminosilicate or molecular sieve composition, facilitates the crystallization procedure.

After crystallization the BeAPO product may be isolated and advantageously washed with water and dried in air. The as-synthesized BeAPO generally contains within its internal pore system at least one form of the templating agent employed in its formation. Most commonly the organic moiety is present, at least in part, as a charge-balancing cation as is generally the case with as-synthesized aluminosilicate zeolites prepared from organic-containing reaction systems. It is possible, however, that some or all of the organic moiety is an occluded molecular species in a particular BeAPO species. As a general rule the templating agent, and hence the occluded organic species, is too large to move freely through the pore system of the BeAPO product and must be removed by calcining the BeAPO at temperatures of 200° C. to 700° C., preferably about 350° C. to about 600° C., to thermally degrade the organic species. In a few instances the pores of the BeAPO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein does not include the condition of the BeAPO phase wherein the organic moiety occupying the intracrystalline pore system as a result of the hydrothermal crystalline process has been reduced by post-synthesis treatment such that the value of "m" in the composition formula

$mR:(Be_xAl_yP_z)O_2$ has a value of less than 0.02. The other symbols of the formula are as defined hereinabove. In those preparations in which an alkoxide is employed as the source of beryllium, aluminum or phosphorus, the corresponding alcohol is necessarily present in the reaction mixture since it is a hydrolysis product of the alkoxide. It has not been determined whether this alcohol participates in the synthesis process as a templating agent. For the purposes of this application, however, this alcohol is arbitrarily omitted from the class of templating agents, even if it is present in the as synthesized BeAPO material.

Since the present BeAPO compositions are formed from $BeO_2$, $AlO_2$, $PO_2$, tetrahedral units which, respectively, have a net charge of $-2$, $-1$ and $+1$, the matter of cation exchangeability is considerably more complicated than in the case of zeolitic molecular sieves in which, ideally, there is a stoichiometric relationship between $AlO_2^-$ tetrahedra and charge-balancing cations. In the instant compositions, an $AlO_2^-$ can be balanced electrically either by association with a $PO_2^+$ tetrahedron or a simple cation such as an alkali metal cation, a cation of beryllium present in the reaction mixture, or an organic cation derived from the templating agent. Similarly, a $BeO_2^{-2}$ tetrahedron can be balanced electrically by association with $PO_2^+$ tetrahedra, a cation of beryllium present in the reaction mixture, a simple cation such as an alkali metal cation, organic cations derived from the templating agent, or other divalent or polyvalent metal cations introduced from an extraneous source. It has also been postulated that nonadjacent $AlO_2^-$ and $PO_2^+$ tetrahedral pairs can be balanced by $Na^+$ and $OH^-$ respectively [Flanigen and Grose, Molecular Sieve Zeolites-I, ACS, Washington, D.C. (1971)].

The BeAPO compositions of the present invention may exhibit cation-exchange capacity when analyzed using ion-exchange techniques heretofore employed with zeolitic aluminosilicates and have pore diameters which are inherent in the lattice structure of each species and which are at least about 3 Å in diameter. Ion exchange of BeAPO compositions is ordinarily possible only after any organic moiety derived from the template, present as a result of synthesis, has been removed from the pore system. Dehydration to remove water present in the as synthesized BeAPO compositions can usually be accomplished, to some degree at least, in the usual manner without removal of the organic moiety, but the absence of the organic species greatly facilitates adsorption and desorption procedures. The BeAPO materials have various degrees of hydrothermal and thermal stability, some being quite remarkable in this regard, and function well as molecular sieve adsorbents and hydrocarbon conversion catalysts or catalyst bases.

In preparing the BeAPO composition it is preferred to use a stainless steel reaction vessel lined with an inert plastic material, e.g., polytetrafluoroethylene, to avoid contamination of the reaction mixture. In general, the final reaction mixture from which each BeAPO composition is crystallized is prepared by forming mixtures of less than all of the reagents and thereafter incorporating into these mixtures additional reagents either singly or in the form of other intermediate mixtures of two or more reagents. In some instances the reagents admixed retain their identity in the intermediate mixture and in other cases some or all of the reagents are involved in chemical reactions to produce new reagents. The term "mixture" is applied in both cases. Further, it ia preferred that the intermediate mixtures as well as the final reaction mixtures be stirred until substantially homogeneous. X-ray patterns of reaction products are obtained by X-ray analysis using either: (1) two computer interfaced Seimen's D-500 X-ray powder diffractometers, available from Seimens Corporation, Cherry Hill, N.J., equipped wit Seimens Type K-805 X-ray sources; or (2) standard X-ray powder diffraction techniques. When the standard technique is employed the radiation source is a high-intensity, copper target, X-ray tube operated at 50 Kv and 40 ma. The diffraction pattern from the copper K-alpha radiation and graphite monochromator is suitably recorded by an X-ray spectrometer scintillation counter, pulse height analyzer and strip chart recorder. X-ray patterns are obtained using flat compressed powder samples which are scanned at 2° (2 theta) per minute, using a two second time constant.

All interplanar spacings (d) in Angstrom units are obtained from the position of the diffraction peaks expressed as 2θ where θ is the Bragg angle as observed on the strip chart. Intensities are determined from the heights of diffraction peaks after subtracting background, "$I_o$" being the intensity of the strongest line or peak, and "I" being the intensity of each of the other peaks.

As will be understood by those skilled in the art the determination of the parameter 2 theta is subject to both human and mechanical error, which in combination, can impose an uncertainty of about ±0.4° on each reported value of 2 theta. This uncertainty is, of course, also manifested in the reported values of the d-spacings, which are calculated from the 2 theta values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, m, w and vw which represent very strong, strong, medium, weak and very weak, respectively.

In certain instances the purity of a synthesized product may be assessed with reference to its X-ray powder diffraction pattern. Thus, for example, if a sample is stated to be pure, it is intended only that the X-ray pattern of the sample is free of lines attributable to crystalline impurities, not that there are no amorphous materials present.

The molecular sieves of the instant invention may be characterized by their X-ray powder diffraction patterns and as such may have one of the X-ray patterns set forth in the following Tables A through V, wherein said X-ray patterns are for the as-synthesized form unless otherwise noted. In most cases, the pattern of the corresponding calcined form will also fall within the relevant Table. However, in some cases the removal of the occluded templating agent which occurs during calcination will be accompanied by sufficient relaxation of the lattice to shift some of the lines slightly outside the ranges specified in the relevant Table. In a small number of cases calcination appears to cause more substantial distortions in the crystal lattice, and hence more significant changes in the X-ray powder diffraction pattern.

TABLE A

| 2θ | (BeAPO-5) d(Å) | Relative Intensity |
|---|---|---|
| 7.3–7.65 | 12.1–11.56 | m–vs |
| 19.5–19.95 | 4.55–4.46 | m–s |
| 20.9–21.3 | 4.25–4.17 | m–vs |
| 22.2–22.6 | 4.00–3.93 | w–vs |
| 25.7–26.15 | 3.47–3.40 | w–m |

TABLE B

| 2θ | (BeAPO-11) d(Å) | Relative Intensity |
|---|---|---|
| 9.3–9.65 | 9.51–9.17 | m–s |
| 20.2–20.6 | 4.40–4.31 | m–s |
| 20.9–21.3 | 4.25–4.17 | s–vs |
| 22.0–22.5 | 4.04–3.95 | m–s |
| 22.5–23.0 | 3.95–3.87 | m–s |
| 23.1–23.4 | 3.85–3.80 | m–vs |

TABLE C

| 2θ | (BeAPO-14) d(Å) | Relative Intensity |
|---|---|---|
| 8.6–8.9 | 10.3–9.93 | vs |

TABLE C-continued

| 2θ | (BeAPO-14) d(Å) | Relative Intensity |
|---|---|---|
| 13.0 | 6.81 | w |
| 21.9–22.2 | 4.06–4.00 | w |
| 25.4 | 3.51 | w |
| 27.5 | 3.24 | w |
| 29.7 | 3.01 | w |

TABLE D

| 2θ | (BeAPO-16) d(Å) | Relative Intensity |
|---|---|---|
| 11.3–11.6 | 7.83–7.63 | m–vs |
| 18.7–18.9 | 4.75–4.70 | w–s |
| 21.9–22.3 | 4.06–3.99 | m–vs |
| 26.5–27.0 | 3.363–3.302 | w–m |
| 29.7–30.05 | 3.008–2.974 | w–m |

TABLE E

| 2θ | (BeAPO-17) d(Å) | Relative Intensity |
|---|---|---|
| 7.7–7.75 | 11.5–11.4 | vs |
| 13.4 | 6.61 | s–vs |
| 15.5–15.55 | 5.72–5.70 | s |
| 19.65–19.7 | 4.52–4.51 | w–s |
| 20.5–20.6 | 4.33–4.31 | vs |
| 31.8–32.00 | 2.812–2.797 | w–s |

TABLE F

| 2θ | (BeAPO-18) d(Å) | Relative Intensity |
|---|---|---|
| 9.6–9.65 | 9.21–9.16 | vs |
| 15.5–15.55 | 5.72–5.70 | m |
| 16.9–17.1 | 5.25–5.19 | m |
| 20.15–20.25 | 4.41–4.39 | m |
| 20.95–21.05 | 4.24–4.22 | m |
| 31.8–32.5 | 2.814–2.755 | m |

TABLE G

| 2θ | (BeAPO-20) d(Å) | Relative Intensity |
|---|---|---|
| 13.7–14.25 | 6.46–6.22 | m–vs |
| 19.55–20.0 | 4.54–4.44 | w–s |
| 24.05–24.6 | 3.70–3.62 | m–vs |
| 34.3–35.0 | 2.614–2.564 | vw–w |
| 42.5–43.1 | 2.127–2.098 | vw–w |

TABLE H

| 2θ | (BeAPO-31) d(Å) | Relative Intensity |
|---|---|---|
| 8.5–8.6 | 10.40–10.28 | m–s |
| 20.2–20.3 | 4.40–4.37 | m |
| 21.9–22.1 | 4.06–4.02 | w–m |
| 22.6–22.7 | 3.93–3.92 | vs |
| 31.7–31.8 | 2.823–2.814 | w–m |

TABLE J*

| 2θ | (BeAPO-33) d(Å) | Relative Intensity |
|---|---|---|
| 9.25–9.55 | 9.56–9.26 | w–m |
| 12.5–12.9 | 7.08–6.86 | vs |
| 16.9–17.3 | 5.25–5.13 | w–m |
| 20.45–20.9 | 4.34–4.25 | w–m |
| 23.85–24.25 | 3.73–3.67 | w–m |
| 26.05–26.35 | 3.42–3.38 | w–m |

TABLE J*-continued

| 2θ | (BeAPO-33) d(Å) | Relative Intensity |
|---|---|---|
| 27.3–27.6 | 3.27–3.23 | vs |

*as-synthesized form

TABLE K*

| 2θ | (BeAPO-33) d(Å) | Relative Intensity |
|---|---|---|
| 13.15–13.4 | 6.73–6.61 | vs |
| 18.05–18.35 | 4.91–4.83 | m |
| 18.4–18.6 | 4.82–4.77 | m |
| 26.55–26.7 | 3.36–3.34 | m |
| 32.0–32.1 | 2.80–2.79 | m |

*calcined form

TABLE L

| 2θ | (BeAPO-34) d(Å) | Relative Intensity |
|---|---|---|
| 9.4–9.8 | 9.41–9.02 | s–vs |
| 15.9–16.5 | 5.57–5.37 | vw–m |
| 17.85–18.6 | 4.97–4.77 | w–s |
| 20.3–21.3 | 4.37–4.17 | m–vs |
| 24.95–25.4 | 3.57–3.41 | vw–s |
| 30.3–30.8 | 2.95–2.81 | w–s |

TABLE M

| 2θ | (BeAPO-35) d(Å) | Relative Intensity |
|---|---|---|
| 10.8–11.1 | 8.19–7.97 | m |
| 17.2–17.4 | 5.16–5.10 | s–vs |
| 21.0–21.25 | 4.23–4.18 | m–s |
| 21.8–22.0 | 4.08–4.04 | vs |
| 31.8–32.2 | 2.814–2.788 | m |

TABLE N

| 2θ | (BeAPO-36) d(Å) | Relative Intensity |
|---|---|---|
| 7.7–8.1 | 11.5–10.9 | vs |
| 16.2–16.7 | 5.47–5.3 | w–m |
| 18.9–19.3 | 4.70–4.60 | m–s |
| 20.6–21.1 | 4.31–4.2 | w–s |
| 21.8–22.0 | 4.08–4.04 | m |

TABLE O

| 2θ | (BeAPO-37) d(Å) | Relative Intensity |
|---|---|---|
| 6.1–6.3 | 14.49–14.03 | vs |
| 15.5–15.7 | 5.72–5.64 | w–m |
| 18.5–18.8 | 4.80–4.72 | w–m |
| 23.5–23.7 | 3.79–3.75 | w–m |
| 26.9–27.1 | 3.31–3.29 | w–m |

TABLE P

| 2θ | (BeAPO-39) d(Å) | Relative Intensity |
|---|---|---|
| 9.4–9.6 | 9.41–9.21 | w–m |
| 13.3–13.6 | 6.66–6.51 | m–vs |
| 18.0–18.4 | 4.93–4.82 | m |
| 21.2–21.5 | 4.19–4.13 | m–s |
| 22.5–23.0 | 3.95–3.87 | s–vs |
| 30.2–30.5 | 2.96–2.93 | w–m |

TABLE Q

| 2θ | (BeAPO-40) d(Å) | Relative Intensity |
|---|---|---|
| 7.5–7.7 | 11.79–11.48 | vw–m |
| 8.0–8.1 | 11.05–10.94 | s–vs |
| 12.4–12.5 | 7.14–7.08 | w–vs |
| 13.6–13.8 | 6.51–6.42 | m–s |
| 14.0–14.1 | 6.33–6.28 | w–m |
| 27.8–28.0 | 3.209–3.187 | w–m |

TABLE R

| 2θ | (BeAPO-41) d(Å) | Relative Intensity |
|---|---|---|
| 13.6–13.8 | 6.51–6.42 | w–m |
| 20.5–20.6 | 4.33–4.31 | w–m |
| 21.1–21.3 | 4.21–4.17 | vs |
| 22.1–22.3 | 4.02–3.99 | m–s |
| 22.8–23.0 | 3.90–3.86 | m |
| 23.1–23.4 | 3.82–3.80 | w–m |
| 25.5–25.9 | 3.493–3.440 | w–m |

TABLE S

| 2θ | (BeAPO-42) d(Å) | Relative Intensity |
|---|---|---|
| 7.15–7.4 | 12.36–11.95 | m–vs |
| 12.5–12.7 | 7.08–6.97 | m–s |
| 21.75–21.9 | 4.09–4.06 | m–s |
| 24.1–24.25 | 3.69–3.67 | vs |
| 27.25–27.4 | 3.273–3.255 | s |
| 30.05–30.25 | 2.974–2.955 | m–s |

TABLE T

| 2θ | (BeAPO-44) d(Å) | Relative Intensity |
|---|---|---|
| 9.4–9.55 | 9.41–9.26 | vs |
| 13.0–13.1 | 6.81–6.76 | w–m |
| 16.0–16.2 | 5.54–5.47 | w–m |
| 20.6–20.85 | 4.31–4.26 | s–vs |
| 24.3–24.4 | 3.66–3.65 | w–vs |
| 30.7–30.95 | 2.912–2.889 | w–s |

TABLE U

| 2θ | (BeAPO-46) d(Å) | Relative Intensity |
|---|---|---|
| 7.2–8.1 | 12.3–10.9 | vs |
| 21.2–21.8 | 4.19–4.08 | w–m |
| 22.5–23.0 | 3.95–3.87 | vw–m |
| 26.6–27.2 | 3.351–3.278 | vw–w |
| 28.5–29.0 | 3.132–3.079 | vw–w |

TABLE V

| 2θ | (BeAPO-47) d(Å) | Relative Intensity |
|---|---|---|
| 9.4 | 9.41 | vs |
| 15.9–16.0 | 5.57–5.54 | w–m |
| 20.5–20.6 | 4.33–4.31 | s |
| 24.5–24.7 | 3.63–3.60 | w |
| 25.8–25.9 | 3.45–3.44 | w |
| 30.4–30.5 | 2.940–2.931 | w |

The following examples are provided to further illustrate the invention and are not intended to be limiting thereof:

EXAMPLE 1

(Preparation of BeAPO-5 and BeAPO-36)

(a) To prepare BeAPO-5 and BeAPO-36, a solution was formed by combining 5.8 grams of 85 wt. percent orthophosphoric acid ($H_3PO_4$) with 14.7 grams of water. To this solution was added 0.8 gram of beryllium sulfate ($BeSO_4.4H_2O$), and the resultant mixture was stirred until the beryllium sulfate had dissolved. 3.1 Grams of hydrated aluminum oxide were then added in the form of a pseudo-boehmite phase comprising 75.1 wt. percent of $Al_2O_3$ and 24.9 wt. percent $H_2O$, and the resultant mixture was stirred until homogeneous. To a 12.1 gram aliquot of this homogeneous mixture was added 1.8 grams of tripropylamine ($Pr_3N$), and the resultant mixture was stirred until homogeneous. The composition of the final reaction mixture thus produced, expressed in terms of the molar oxide ratios of the components of the reaction mixture, was: 1.0 $Pr_3N$:0.17 BeO:0.92 $Al_2O_3$:1.00 $P_2O_5$:40 $H_2O$.

This final reaction mixture was digested by sealing it in a stainless steel pressure vessel lined with polytetrafluoroethylene and heating it in an oven at 150° C. under autogenous pressure for 72 hours. The solid reaction product (which was determined by the analyses described below to be a mixture of BeAPO-5 and BeAPO-36) was recovered by filtration, washed with water and dried in air at ambient temperature.

A sample of this solid reaction product was analyzed and the following chemical analysis obtained:

| Component | Weight percent |
|---|---|
| Carbon | 6.3 |
| Nitrogen | 0.90 |
| BeO | 1.7 |
| $Al_2O_3$ | 33.8 |
| $P_2O_5$ | 51.7 |
| LOI* | 13.4 |

*LOI indicates loss on ignition.

The above chemical analysis corresponds to a product composition in molar oxide ratios of:

0.16 $Pr_3N$:0.19 BeO:0.91 $al_2O_3$:1.0 $P_2O_5$:0.76 $H_2O$ which corresponds to an empirical chemical formula (on an anhydrous basis) of: 0.04 $Pr_3N$:($Be_{0.05}Al_{0.45}P_{0.50})O_2$ so that the product contained beryllium, aluminum and phosphorus in amounts within the hexagonal compositional area defined by points A, B, C, D, E and F of FIG. 1.

The X-ray powder diffraction pattern of the product, as synthesized, was characterized by the data in the following Tables AA and NA. (Hereinafter, Tables designated AA, AB etc. are Tables of X-ray data which include all the peaks mentioned in Table A above, and similarly for Tables designated BA, BB etc.) The peaks from BeAPO-5 AND BeAPO-36 were separated by comparison of the X-ray powder diffraction pattern with patterns for materials of similar structure, such as the materials described in the aforementioned U.S. Pat. Nos. 4,500,651; 4,567,029 and 4,544,143.

TABLE AA (BeAPO-5)

| $2\theta$ | d(Å) | Relative Intensity $100 \times I/I_o$ |
|---|---|---|
| 7.53 | 11.74 | 100 |
| 13.0 | 6.81 | 11 |
| 15.0 | 5.91 | 19 |

TABLE AA-continued (BeAPO-5)

| $2\theta$ | d(Å) | Relative Intensity $100 \times I/I_o$ |
|---|---|---|
| 19.9 | 4.46 | 45 |
| 21.4 | 4.15 | 13 |
| 22.6 | 3.93 | 61 |
| 24.2 | 3.68 | 5* |
| 26.1 | 3.41 | 30 |
| 29.3 | 3.05 | 9 |
| 30.2 | 2.959 | 19 |
| 34.7 | 2.585 | 14 |
| 38.1 | 2.362 | 3 |
| 47.9 | 1.899 | 5 |

*Intensity increased significantly by peak overlap

TABLE NA (BeAPO-36)

| $2\theta$ | d(Å) | Relative Intensity $100 \times I/I_o$ |
|---|---|---|
| 8.04 | 11.00 | 100 |
| 16.7 | 5.31 | 33 |
| 19.3 | 4.60 | 46* |
| 21.1 | 4.21 | 63* |
| 22.0 | 4.04 | 24* |
| 24.2 | 3.68 | 33* |
| 27.6 | 3.23 | 19 |
| 32.4 | 2.763 | 20 |
| 35.1 | 2.557 | 19* |

*Intensity increased significantly by peak overlap

The X-ray powder diffraction pattern of the product, after calcination and the McBain adsorption studies described below, was characterized by the data in the following Table AB:

TABLE AB (BeAPO-5)

| $2\theta$ | d(Å) | Relative Intensity $100 \times I/I_o$ |
|---|---|---|
| 7.37 | 11.99 | 100 |
| 7.86* | 11.25 | 12 |
| 12.8 | 6.91 | 12 |
| 14.9 | 5.94 | 7 |
| 16.6* | 5.34 | 2 |
| 19.3* | 4.60 | 5 |
| 19.8 | 4.49 | 21 |
| 21.3 | 4.17 | 15 |
| 22.5 | 3.95 | 35 |
| 26.0 | 3.43 | 14 |
| 29.2 | 3.06 | 6 |
| 30.1 | 2.97 | 10 |
| 34.7 | 2.59 | 7 |
| 38.1 | 2.36 | 2 |
| 48.0 | 1.90 | 2 |

*Peak due to BeAPO-36

(b) A sample of the product produced in part (a) was calcined and used in the n-butane cracking tests described in Example 9 below. Following these cracking tests, the sample was utilized in adsorption capacity studies using a standard McBain-Bakr gravimetric adsorption apparatus. After the cracking tests, but before being used in the adsorption tests, the sample was activated by heating to 350° C. for 16 hours in vacuum, and this activation was repeated before each new adsorbate. The following data were generated in the adsorption studies:

| Adsorbate | Kinetic Diameter (Å) | Pressure (Torr) | Temp, °C. | Wt. % Adsorbed |
|---|---|---|---|---|
| $O_2$ | 3.46 | 100 | −183 | 13.3 |

| Adsorbate | Kinetic Diameter (Å) | Pressure (Torr) | Temp, °C. | Wt. % Adsorbed |
|---|---|---|---|---|
| Neopentane | 6.2 | 300 | 22 | 3.8 |
| H₂O | 2.65 | 4.6 | 22 | 14.6 |
| n-hexane | 4.3 | 45 | 22 | 6.3 |

From the above data, the pore size of the calcined product was determined to be greater than about 6.2 Å, as shown by the adsorption of neopentane (kinetic diameter of 6.2 Å).

EXAMPLE 2

Preparation of BeAPO-11)

(a) To prepare BeAPO-11, a solution was formed by combining 11.6 grams of 85 wt. percent orthophosphoric acid ($H_3PO_4$) with 28.8 grams of water. To this solution were added 3.5 grams of beryllium sulfate (Be-$SO_4 \cdot 4H_2O$), and the resultant mixture was stirred until the beryllium sulfate had dissolved. 5.4 Grams of hydrated aluminum oxide were then added in the form of a pseudo-boehmite phase comprising 75.1 wt. percent of $Al_2O_3$ and 24.9 wt. percent $H_2O$, and the resultant mixture was stirred until homogeneous. To a 12.0 gram aliquot of this homogeneous mixture was added 1.3 grams of di-n-propylamire (n-$Pr_2NH$), and the resultant mixture was stirred until homogeneous. The composition of the final reaction mixture thus produced, expressed in terms of the molar oxide ratios of the components of the reaction mixture, was: 1.0 n-$Pr_2NH$:0.40 BeO:0.80 $Al_2O_3$:1.0 $P_2O_5$:40 $H_2O$.

This final reaction mixture was digested by sealing it in a stainless steel pressure vessel lined with polytetrafluoroethylene and heating it in an oven at 150° C. under autogenous pressure for 64 hours. The solid reaction product (which was determined by the analyses described below to be BeAPO-11) was recovered by filtration, washed with water and dried in air at ambient temperature.

A sample of this solid reaction product was analyzed and the following chemical analysis obtained:

| Component | Weight percent |
|---|---|
| Carbon | 4.7 |
| Nitrogen | 0.86 |
| BeO | 3.03 |
| $Al_2O_3$ | 30.8 |
| $P_2O_5$ | 53.9 |
| LOI* | 11.4 |

*LOI indicates loss on ignition.

The above chemical analysis corresponds to a product composition in molar oxide ratios of: 0.17 n-$Pr_2NH$:0.32 BeO:0.80 $Al_2O_3$:1.0 $P_2O_5$:0.70 $H_2O$ which corresponds to an empirical chemical formula (on an anhydrous basis) of: 0.04 n-$Pr_2NH$:($Be_{0.08}Al_{0.41}P_{0.51}$)$O_2$ so that the product contained beryllium, aluminum and phosphorus in amounts within the hexagonal compositional area defined by points A, B, C, D, E and F of FIG. 1.

The X-ray powder diffraction pattern of the product, as synthesized, was characterized by the data in the following Table BA:

TABLE BA (BeAPO-11)

| 2θ | d(Å) | Relative Intensity 100 × I/I₀ |
|---|---|---|
| 8.11 | 10.90 | 43 |
| 9.47 | 9.34 | 58 |
| 13.2 | 6.71 | 21 |
| 15.7 | 5.64 | 38 |
| 16.3 | 5.44 | 6 |
| 19.1 | 4.65 | 6 |
| 20.4 | 4.35 | 56 |
| 21.3 | 4.17 | 100 |
| 22.3 | 3.99 | 58 |
| 22.6 | 3.93 | 54 |
| 22.9 | 3.88 | 65 |
| 23.3 | 3.82 | 86 |
| 24.6 | 3.62 | 7 |
| 24.8 | 3.59 | 8 |
| 25.2 | 3.53 | 6 |
| 26.6 | 3.35 | 38 |
| 28.3 | 3.15 | 6 |
| 28.8 | 3.10 | 19 |
| 29.1 | 3.07 | 6 |
| 29.7 | 3.01 | 8 |
| 31.7 | 2.82 | 10 |
| 32.9 | 2.72 | 22 |
| 34.4 | 2.61 | 11 |
| 36.5 | 2.47 | 6 |
| 38.0 | 2.37 | 9 |
| 39.5 | 2.28 | 4 |
| 43.4 | 2.08 | 4 |
| 44.9 | 2.02 | 7 |
| 50.9 | 1.79 | 6 |

The X-ray powder diffraction pattern of the product, after calcination and the McBain adsorption studies described below, was characterized by the data in the following Table BB:

TABLE BB (BeAPO-11)

| 2θ | d(Å) | Relative Intensity 100 × I/I₀ |
|---|---|---|
| 8.11 | 10.90 | 50 |
| 9.56 | 9.25 | 50 |
| 13.1 | 6.76 | 24 |
| 15.8 | 5.61 | 50 |
| 20.3 | 4.37 | 32 |
| 21.4 | 4.15 | 100 |
| 22.4 | 3.97 | 69 |
| 23.0 | 3.87 | 52 |
| 23.4 | 3.80 | 56 |
| 24.5 | 3.63 | 4 |
| 25.0 | 3.56 | 5 |
| 26.5 | 3.36 | 19 |
| 26.7 | 3.34 | 14 |
| 29.0 | 3.08 | 16 |
| 29.7 | 3.01 | 9 |
| 31.9 | 2.81 | 10 |
| 32.9 | 2.72 | 15 |
| 34.6 | 2.59 | 5 |
| 36.4 | 2.47 | 7 |
| 38.2 | 2.36 | 9 |
| 43.6 | 2.08 | 3 |
| 45.0 | 2.01 | 4 |

(b) A sample of the product produced in part (a) was calcined and used in the n-butane cracking tests described in Example 10 below. Following these cracking tests, the sample was utilized in adsorption capacity studies using a standard McBain-Bakr gravimetric adsorption apparatus. After the cracking tests, but before being used in the adsorption tests, the sample was activated by heating to 350° C. for 16 hours in vacuum, and this activation was repeated before each new adsorbate.

The following data were generated in the adsorption studies:

| Adsorbate | Kinetic Diameter (Å) | Pressure (Torr) | Temp, °C | Wt. % Adsorbed |
|---|---|---|---|---|
| $O_2$ | 3.46 | 100 | −183 | 1.9 |
| $H_2O$ | 2.65 | 4.6 | 22 | 8.9 |
| n-Hexane | 4.3 | 45 | 22 | 0.5 |

From the above data, the pore size of the calcined product was determined to be greater than about 2.65 Å, as shown by the adsorption of water (kinetic diameter of 2.65 Å). The low adsorptions of oxygen and n-hexane (kinetic diameters of 3.46 and 4.3 Å respectively) are apparently due to pore blockage since the structural type to which BeAPO-11 belongs is known to have a pore size of about 6.0 Å.

EXAMPLE 3

(Preparation of BeAPO-17)

(a) BeAPO-17 is prepared from a reaction mixture having a composition, expressed in terms of the molar oxide ratios of the components of the reaction mixture, of: 1.0–2.0 QN:0.1–0.4 BeO:0.5–1.0 $Al_2O_3$:0.5–1.0 $P_2O_5$:40–100 $H_2O$ where "QN" denotes quinuclidine.

The reaction mixture is digested by placing the reaction mixture in a sealed stainless steel pressure vessel and heating it at an effective temperature and for an effective time until crystals of the BeAPO-17 product are obtained. Solids are then recovered by filtration, washed with water and dried in air at room temperature.

The BeAPO-17 product's chemical analysis shows the BeAPO-17 product contains beryllium, aluminum and phosphorus in amounts within the hexagonal compositional area defined by points A, B, C., E and F of FIG. 1.

The X-ray powder diffraction pattern of a BeAPO-17 product is characterized by the following data:

| $2\theta$ | d(Å) | Relative Intensity |
|---|---|---|
| 7.7–7.75 | 11.5–11.4 | vs |
| 13.4 | 6.61 | s–vs |
| 15.5–15.55 | 5.72–5.70 | s |
| 19.65–19.7 | 4.52–4.51 | w–s |
| 20.5–20.6 | 4.33–4.31 | vs |
| 31.8–32.00 | 2.812–2.797 | w–s |

(b) The X-ray powder diffraction pattern for a calcined BeAPO-17 is also characterized by the X-ray pattern of part (a).

(c) When the calcined BeAPO-17 of part (b) is utilized in adsorption capacity studies using a standard McBain-Bakr gravimetric adsorption apparatus the measurements are made on a sample after activation at 350° C. in a vacuum. The following data are used in the adsorption studies:

| Adsorbate | Kinetic Diameter (Å) | Pressure (Torr) | Temp, °C | Wt. % Adsorbed* |
|---|---|---|---|---|
| $O_2$ | 3.46 | 100 | −183 | 10 |
| $O_2$ | 3.46 | 750 | −183 | 12 |
| n-butane | 4.3 | 100 | 24 | 4 |
| $H_2O$ | 2.65 | 4.3 | 24 | 13 |
| $H_2O$ | 2.65 | 20 | 24 | 14 |

*typical amount adsorbed

The pore diameter of BeAPO-17 is about 4.3 Å.

EXAMPLE 4 (Preparation of BeAPO-31)

(a) BeAPO-31 is prepared from a reaction mixture having a composition, expressed in terms of the molar oxide ratios of the components of the reaction mixture, of: 1.0–2.0 DPA:0.1–0.4 BeO:0.5–1.0 $Al_2O_3$:0.5–1.0 $P_2O_5$:40–100 $H_2O$ where "DPA" denotes di-n-propylamine.

The reaction mixture is seeded with crystals of AlPO$_4$-31 (U.S. Pat. No. 4,310,440) and digested by placing the reaction mixture in a sealed stainless steel pressure vessel and heating it at an effective temperature and for an effective time until crystals of the BeAPO-31 product are obtained. Solids are then recovered by filtration, washed with water and dried in air at room temperature.

The BeAPO-31 product's chemical analysis shows the BeAPO-31 product contains beryllium, aluminum and phosphorus in amounts within the hexagonal compositional area defined by points A, B, C, D, E and F of FIG. 1.

The X-ray powder diffraction pattern of a BeAPO-31 product is characterized by the following data:

| $2\theta$ | d(Å) | Relative Intensity |
|---|---|---|
| 8.5–8.6 | 10.40–10.28 | m–s |
| 20.2–20.3 | 4.40–4.37 | m |
| 21.9–22.1 | 4.06–4.02 | w–m |
| 22.6–22.7 | 3.93–3.92 | vs |
| 31.7–31.8 | 2.823–2.814 | w–m |

(b) The X-ray powder diffraction pattern for a calcined BeAPO-31 is also characterized by the x-ray pattern of part (a).

(c) When the calcined BeAPO-31 of part (b) is utilized in adsorption capacity studies using a standard McBain-Bakr gravimetric adsorption apparatus the measurements are made on a sample after activation at 350° C. in a vacuum. The following data are used in the adsorption studies:

| Adsorbate | Kinetic Diameter (Å) | Pressure (Torr) | Temp, °C | Wt. % Adsorbed* |
|---|---|---|---|---|
| $O_2$ | 3.46 | 100 | −183 | 4 |
| $O_2$ | 3.46 | 750 | −183 | 6 |
| Cyclohexane | 6.0 | 90 | 24 | 3 |
| Neopentane | 6.2 | 700 | 24 | 3 |
| $H_2O$ | 2.65 | 4.3 | 24 | 3 |
| $H_2O$ | 2.65 | 20 | 24 | 10 |

*typical amount adsorbed

The pore diameter of BeAPO-31 is greater than about 6.2 Å.

EXAMPLE 5

(Preparation of BeAPO-34)

(a) To prepare BeAPO-34, a solution was formed by combining 5.8 grams of 85 wt. percent orthophosphoric acid ($H_3PO_4$) with 8.9 grams of water. To this solution were added 1.8 grams of beryllium sulfate (BeSO$_4$.4-H$_2$O), and the resultant mixture was stirred until the beryllium sulfate had dissolved. 2.7 Grams of hydrated aluminum oxide were then added in the form of a pseudo-boehmite phase comprising 75.1 wt. percent of Al$_2$O$_3$ and 24.9 wt. percent of H$_2$O, and the resultant mixture was stirred until homogeneous. To this homogeneous mixture was added 9.2 grams of 40 wt. percent tetraethylammonium hydroxide (Et$_4$NOH), and the resultant mixture was stirred until homogeneous. The composition of the final reaction mixture thus produced, expressed in terms of the molar oxide ratios of the components of the reaction mixture, was: 1.0 Et$_4$NOH:0.40 BeO:0.80 Al$_2$O$_3$:1.0 P$_2$O$_5$:40 H$_2$O.

A 14.9 gram aliquot of this final reaction mixture was digested by sealing it in a stainless steel pressure vessel lined with polytetrafluoroethylene and heating it in an oven at 100° C. under autogenous pressure for 68 hours. The solid reaction product (which was determined by the analyses described below to be BeAPO-34) was recovered by filtration, washed with water and dried in air at ambient temperature.

A sample of this solid reaction product was analyzed and the following chemical analysis obtained:

| Component | Weight percent |
| --- | --- |
| Carbon | 9.9 |
| Nitrogen | 1.5 |
| BeO | 3.5 |
| Al$_2$O$_3$ | 29.0 |
| P$_2$O$_5$ | 46.4 |
| LOI* | 20.6 |

*LOI indicates loss on ignition.

The above chemical analysis corresponds to a product composition in molar oxide ratios of: 0.32 Et$_4$NOH:0.43 BeO:0.87 Al$_2$O$_3$:1.0 P$_2$O$_5$:0.87 H$_2$O which corresponds to an empirical chemical formula (on an anhydrous basis) of: 0.08 TEAOH: (Be$_{0.10}$Al$_{0.42}$P$_{0.48}$)O$_2$ so that the product contained beryllium, aluminum and phosphorus in amounts within the hexagonal compositional area defined by points A, B, C, D, E and F of FIG. 1.

The X-ray powder diffraction pattern of the product, as synthesized, was characterized by the data in the following Table LA:

TABLE LA

| (BeAPO-34) | | |
| --- | --- | --- |
| 2θ | d(Å) | Relative Intensity 100 × I/I$_o$ |
| 9.74 | 9.08 | 87 |
| 13.1 | 6.76 | 16 |
| 14.4 | 6.15 | 17 |
| 16.3 | 5.44 | 52 |
| 18.4 | 4.82 | 28 |
| 21.0 | 4.23 | 100 |
| 22.7 | 3.92 | 5 |
| 23.5 | 3.79 | 8 |
| 25.7 | 3.47 | 27 |
| 26.3 | 3.39 | 18 |
| 28.1 | 3.18 | 4 |
| 28.9 | 3.09 | 4 |
| 30.1 | 2.97 | 5 |
| 31.1 | 2.88 | 34 |
| 31.8 | 2.81 | 22 |
| 35.0 | 2.56 | 6 |
| 37.0 | 2.43 | 4 |
| 40.4 | 2.23 | 5 |
| 44.2 | 2.05 | 6 |
| 48.4 | 1.88 | 5 |
| 49.8 | 1.83 | 6 |

TABLE LA-continued

| (BeAPO-34) | | |
| --- | --- | --- |
| 2θ | d(Å) | Relative Intensity 100 × I/I$_o$ |
| 51.9 | 1.76 | 4 |
| 54.0 | 1.70 | 3 |
| 55.5 | 1.66 | 2 |

The X-ray powder diffraction pattern of the product, after calcination by heating to 500° C. for 2 hours under nitrogen, was characterized by the data in the following Table LB:

TABLE LB

| (BeAPO-34) | | |
| --- | --- | --- |
| 2θ | d(Å) | Relative Intensity 100 × I/I$_o$ |
| 9.78 | 9.04 | 100 |
| 13.2 | 6.71 | 43 |
| 16.4 | 5.41 | 16 |
| 18.4 | 4.82 | 9 |
| 21.2 | 4.19 | 40 |
| 25.7 | 3.47 | 10 |
| 26.7 | 3.34 | 15 |
| 31.5 | 2.84 | 19 |

EXAMPLE 6

(Preparation of BeAPO-34)

(a) To prepare BeAPO-34, a solution was formed by combining 23.1 grams of 85 wt. percent orthophosphoric acid (H$_3$PO$_4$) with 35.5 grams of water. To this solution were added 7.1 grams of beryllium sulfate (BeSO$_4$. 4H$_2$O), and the resultant mixture was stirred until the beryllium sulfate had dissolved. 10.9 Grams of hydrated aluminum oxide were then added in the form of a pseudo-boehmite phase comprising 75.1 wt. percent of Al$_2$O$_3$ and 24.9 wt. percent of H$_2$O, and the resultant mixture was stirred until homogeneous. To this homogeneous mixture were added 36.8 grams of 40 wt. percent tetraethylammonium hydroxide (Et$_4$NOH), and the resultant mixture was stirred until homogeneous. The composition of the final reaction mixture thus produced, expressed in terms of the molar oxide ratios of the components of the reaction mixture, was: 1.0 Et$_4$NOH:0.40 BeO:0.80 Al$_2$O$_3$:1.0 P$_2$O$_5$:40 H$_2$O.

A 96.7 gram aliquot of this final reaction mixture was digested by sealing it in a stainless steel pressure vessel lined with polytetrafluoroethylene and heating it in an oven at 100° C. under autogenous pressure for 66 hours. The solid reaction product (which was determined by the analyses described below to be BeAPO-34) was recovered by filtration, washed with water and dried in air at ambient temperature.

A sample of this solid reaction product was analyzed and the following chemical analysis obtained:

| Component | Weight percent |
| --- | --- |
| Carbon | 9.7 |
| Nitrogen | 1.3 |
| BeO | 3.1 |
| Al$_2$O$_3$ | 27.6 |
| P$_2$O$_5$ | 47.5 |
| LOI* | 22.9 |

*LOI indicates loss on ignition.

The above chemical analysis corresponds to a product composition in molar oxide ratios of: 0.30 Et$_4$ NOH:0.37 BeO:0.81 Al$_2$O$_3$:1.0 P$_2$O$_5$:1.32 H$_2$O which corresponds to an empirical chemical formula (on an anhydrous basis) of: 0.08 TEAOH:(Be$_{0.09}$Al$_{0.44}$P$_{0.50}$)O$_2$ so that the product contained beryllium, aluminum and phosphorus in amounts within the hexagonal compositional area defined by points A, B, C, D, E and F of FIG. 1.

The X-ray powder diffraction pattern of the product, as synthesized, was essentially identical to that of the as-synthesized product of Example 5 above. The X-ray powder diffraction pattern of the product, after calcination by heating from ambient temperature to 500° C. over a period of 4 hours in air, then holding at 500° C. for 2 hours in air, was characterized by the data in the following Table LC:

TABLE LC

| 2θ | d(Å) | (BeAPO-34) Relative Intensity 100 × I/I$_o$ |
|---|---|---|
| 9.80 | 9.03 | 100 |
| 13.2 | 6.71 | 34 |
| 16.5 | 5.37 | 16 |
| 18.6 | 4.77 | 9 |
| 21.3 | 4.17 | 36 |
| 26.1 | 3.41 | 10 |
| 26.7 | 3.34 | 14 |
| 31.6 | 2.83 | 19 |

(b) A sample of the product produced in part (a) was utilized in adsorption capacity studies using a standard McBain-Bakr gravimetric adsorption apparatus. Before being used in the adsorption tests, the sample was activated by heating to 425° C. for 16 hours under vacuum. The following data were generated in the adsorption studies:

| Adsorbate | Kinetic Diameter (Å) | Pressure (Torr) | Temp, °C. | Wt. % Adsorbed |
|---|---|---|---|---|
| O$_2$ | 3.46 | 100 | −183 | 21.5 |
| n-Hexane | 4.3 | 50 | 22 | 2.6 |
| Neopentane | 6.2 | 299 | 22 | 0.1 |

From the above data, the pore size of the calcined product was determined to be greater than about 4.3 Å, as shown by the adsorption of n-hexane (kinetic diameter of 4.3 Å), and less than about 6.2 Å as shown by the negligible adsorption of neopentane (kinetic diameter of 6.2 Å).

Other specimens of BeAPO-34 (as-synthesized) prepared in a similar manner has x-ray powder diffraction patterns similar to that given in Table LA above. The following general Table LD summarizes the X-ray powder diffraction lines which were obtained from the various specimens of BeAPO-34; the least intense lines were not obtained from every specimen.

TABLE LD

| 2θ | d(Å) | (BeAPO-34) Relative Intensity 100 × I/I$_o$ |
|---|---|---|
| 9.53–9.74 | 9.27–9.07 | 87–100 |
| 12.9–13.1 | 6.86–6.75 | 16–17 |
| 14.2–14.4 | 6.23–6.15 | 16–19 |
| 16.1–16.3 | 5.50–5.43 | 54–61 |
| 18.1–18.4 | 4.90–4.82 | 24–28 |
| 20.6–21.0 | 4.31–4.23 | 100 |
| 22.4–22.7 | 3.97–3.91 | 4–10 |
| 23.3–23.5 | 3.81–3.78 | 0–8 |
| 25.5–25.7 | 3.49–3.46 | 25–27 |
| 26.1–26.3 | 3.41–3.39 | 18–20 |
| 27.9–28.1 | 3.20–3.17 | 4–5 |
| 28.7–28.9 | 3.11–3.09 | 3–4 |
| 29.9–30.1 | 2.99–2.97 | 5–6 |
| 30.9–31.1 | 2.891–2.873 | 30–34 |
| 31.6–31.8 | 2.829–2.811 | 21–22 |
| 34.8–35.0 | 2.576–2.561 | 5–6 |
| 36.8–37.0 | 2.440–2.427 | 3–4 |
| 40.2–40.4 | 2.241–2.231 | 0–5 |
| 44.0–44.2 | 2.056–2.047 | 6 |
| 48.2–48.4 | 1.886–1.879 | 4–5 |
| 49.7–49.8 | 1.833–1.829 | 0–8 |
| 51.7–51.9 | 1.766–1.760 | 3–4 |
| 53.9–54.0 | 1.700–1.697 | 3 |
| 55.3–55.5 | 1.660–1.654 | 0–3 |

EXAMPLE 7

(Preparation of BeAPO-44)

(a) BeAPO-44 is prepared from a reaction mixture having a composition, expressed in terms of the molar oxide ratios of the components of the reaction mixture, of: 1.0–2.0 CHA:0.1–0.4 BEO:0.5–1.0 Al$_2$O$_3$:0.5–1.0 P$_2$O$_5$:40–100 H$_2$O where "CHA" denotes cyclohexylamine.

The reaction mixture is digested by placing the reaction mixture in a sealed stainless steel pressure vessel and heating it at an effective temperature and for an effective time until crystals of the BeAPO-44 product are obtained. Solids are then recovered by filtration, washed with water and dried in air at room temperature.

The BeAPO-44 product's chemical analysis shows the BeAPO-44 product contains beryllium, aluminium and phosphorous in amounts within the hexagonal compositional area defined by points A, B, C, D, E and F of FIG. 1.

the X-ray powder diffraction pattern of a BeAPO-44 product is characterized by the following data:

| 2θ | d(Å) | Relative Intensity |
|---|---|---|
| 9.4–9.55 | 9.41–9.26 | vs |
| 13.0–13.1 | 6.81–6.76 | w-m |
| 16.0–16.2 | 5.54–5.47 | w-m |
| 20.6–20.85 | 4.31–4.26 | s-vs |
| 24.3–24.4 | 3.66–3.65 | w-vs |
| 30.7–30.95 | 2.912–2.889 | w-s |

(b) When the calcined BeAPO-44 is utilized in adsorption capacity studies using a standard McBain-bakr gravimetric adsorption apparatus the measurements are made on a sample after activation at 350° C. in a vacuum. The following data are used in the adsorption studies:

| Adsorbate | Kinetic Diameter (Å) | Pressure (Torr) | Temp, °C. | Wt. % Adsorbed* |
|---|---|---|---|---|
| O$_2$ | 3.46 | 100 | −183 | 13 |
| O$_2$ | 3.46 | 750 | −183 | 16 |
| n-hexane | 4.3 | 100 | 24 | 2 |
| H$_2$O | 2.65 | 4.3 | 24 | 15 |
| H$_2$O | 2.65 | 20 | 24 | 17 |

*typical amount adsorbed

The pore diameter of BeAPO-44 is about 4.3Å.

EXAMPLE 8

(Preparation of BeAPO-20)

(a) To prepare BeAPO-20, a solution was formed by combining 5.8 grams of 85 wt. percent orthophosphoric acid ($H_3PO_4$) with 14.7 grams of water. To the solution was added 0.8 gram of beryllium sulfate ($BeSO_4.4H_2O$), and the resultant mixture was stirred until the beryllium sulfate had dissolved. 3.1 Grams of hydrated aluminum oxide were then added in the form of a pseudo-boehmite phase comprising 75.1 wt. percent of $Al_2O_3$ and 24.9 wt. percent $H_2O$, and the resultant mixture was stirred until homogeneous. To an 11.8 gram aliquot of this homogeneous mixture were added 2.3 grams of tetramethylammonium hydroxide ($TMAOH.5H_2O$), and the resultant mixture was stirred until homogeneous. The composition of the final reaction mixture thus produced, expressed in terms of the molar oxide ratios of the components of the reaction mixture, was: 1.1 TMAOH:0.17 BeO:0.92 $Al_2O_3$:1.0 $P_2O_5$:40 $H_2O$.

This final reaction mixture was digested by sealing it in a stainless steel pressure vessel lined with polytetrafluoroethylene and heating it in an oven at 150° C. under autogenous pressure for 72 hours. The solid reaction product (which was determined by the analyses described below to be BeAPO-20) was recovered by centrifugation, washed with water and dried in air at ambient temperature.

A sample of this solid reaction product was analyzed and the following chemical analysis obtained:

| Component | Weight percent |
| --- | --- |
| Carbon | 7.3 |
| Nitrogen | 2.1 |
| BeO | 1.53 |
| $Al_2O_3$ | 30.0 |
| $P_2O_5$ | 47.7 |
| LOI* | 20.6 |

*LOI indicates loss on ignition.

The above chemical analysis corresponds to a product composition in molar oxide ratios of: 0.45 TMAOH:0.18 BeO:0.88 $Al_2O_3$:1.0 $P_2O_5$:1.1 $H_2O$ which corresponds to an empirical chemical formula (on an anhydrous basis) of: 0.123 TMAOH:($Be_{0.046}al_{0.445}P_{0.508})O_2$ so that the product contained beryllium, aluminum and phosphorus in amounts within the hexagonal compositional area defined by points A, B, C, D, E and F of FIG. 1.

The X-ray powder diffraction pattern of the product, as synthesized, was characterized by the data in the following Table GA:

TABLE GA (BeAPO-20)

| $2\theta$ | d(Å) | Relative Intensity $100 \times I/I_o$ |
| --- | --- | --- |
| 14.1 | 6.28 | 63 |
| 20.0 | 4.44 | 45 |
| 22.4 | 3.97 | 11 |
| 24.5 | 3.63 | 100 |
| 28.3 | 3.15 | 17 |
| 31.8 | 2.81 | 11 |
| 34.9 | 2.57 | 16 |
| 40.5 | 2.23 | 3* |
| 40.8 | 2.21 | 3* |
| 43.1 | 2.10 | 7* |
| 43.5 | 2.08 | 5* |
| 47.8 | 1.90 | 4* |
| 48.2 | 1.89 | 4* |
| 52.3 | 1.75 | 9* |
| 52.9 | 1.73 | 5* |

*These four pairs of peaks probably indicate that the BeAPO-20 contains a minor proportion of $AlPO_4$-20 (see U.S. Pat. No. 4,310,440).

X-ray powder diffraction pattern of the product, after calcination and the McBain adsorption studies described below, was characterized by the data in the following Table GB:

TABLE GB (BeAPO-20)

| $2\theta$ | d(Å) | Relative Intensity $100 \times I/I_o$ |
| --- | --- | --- |
| 14.1 | 6.28 | 100 |
| 20.0 | 4.44 | 42 |
| 22.5 | 3.95 | 12 |
| 24.6 | 3.62 | 97 |
| 28.4 | 3.14 | 16 |
| 31.8 | 2.81 | 14 |
| 35.0 | 2.56 | 15 |
| 40.5 | 2.23 | 3 |
| 43.1 | 2.10 | 5 |
| 48.2 | 1.89 | 3 |
| 52.5 | 1.74 | 8 |

(b) A sample of the product produced in part (a) was calcined and used in the n-butane cracking tests described in example 12 below. Following these cracking tests, the sample was utilized in adsorption capacity studies using a standard McBain-Bakr gravimetric adsorption apparatus. After the cracking tests, but before being used in the adsorption tests, the sample was activated by heating to 350° C. for 16 hours in vacuum, and this activation was repeated before each new adsorbate. The following data were generated in the adsorption studies:

| Adsorbate | Kinetic Diameter (Å) | Pressure (Torr) | Temp, °C. | Wt. % Adsorbed |
| --- | --- | --- | --- | --- |
| $O_2$ | 3.46 | 100 | −183 | 1.5 |
| $H_2O$ | 2.65 | 4.6 | 22 | 11.6 |

From the above data, the pore size of the calcined product was determined to be greater than about 2.65 Å, as shown by the adsorption of water (kinetic diameter of 2.65 Å), and less than about 3.46 Å as shown by the low adsorption of oxygen (kinetic diameter of 3.46 Å).

PROCESS APPLICATIONS

The BeAPO compositions of the present invention are, in general, hydrophilic and adsorb water preferentially over common hydrocarbon molecules such as paraffins, olefins and aromatic species, e.g., benzene, xylenes and cumene. Thus the present molecular sieve compositions as a class are useful as desiccants in such adsorption separation/purification processes as natural gas drying, cracked gas drying. Water is also preferentially adsorbed over the so-called permanent gases such as carbon dioxide, nitrogen, oxygen and hydrogen. These BeAPOs are therefore suitably employed in the drying of reformer hydrogen streams and in the drying of oxygen, nitrogen or air prior to liquefaction.

The present BeAPO compositions also exhibit novel surface selectivity characteristics which render them useful as catalyst or catalyst bases in a number of hydrocarbon conversion and oxidative combustion reactions. They can be impregnated or otherwise loaded with catalytically active metals by methods well known in the art (e.g. ion exchange or impregnation) and used, for example, in fabricating catalyst compositions having silica or alumina bases. The pore diameters of the BeAPO compositions range from less than 3.46 Å to greater than 6.2 Å; those species having pores larger than about 4Å are preferred for catalytic applications.

Among the hydrocarbon conversion reactions catalyzed by BeAPO compositions are cracking, hydrocracking, alkylation for both the aromatic and isoparaffin types, isomerization including xylene isomerization, polymerization, reforming, hydrogenation, dehydrogenation, transalkylation, dealkylation, hydrodecyclization and dehydrocyclization.

Using BeAPO catalyst compositions which contain a hydrogenation promoter such as platinum or palladium, heavy petroleum residual stocks, cyclic stocks and other hydrocrackable charge stocks, can be hydrocracked at temperatures in the range of 400° F. to 825° F. (204° C. to 441° C.) using molar ratios of hydrogen to hydrocarbon in the range of between 2 and 80, pressures between 10 and 3500 p.s.i.g. (0.171 to 24.23 MPa.), and a liquid hourly space velocity (LHSV) of from 0.1 to 20, preferably 1.0 to 10.

The BeAPO catalyst compositions employed i hydrocracking are also suitable for use in reforming processed in which the hydrocarbon feedstocks contact the catalyst at temperatures of from about 700° F. to 1000° F. (371° C. to 538° C.), hydrogen pressures of from 100 to 500 p.s.i.g. (0.791 to 3.448 MPa.), LHSV values in the range of 0.1 to 10 and hydrogen to hydrocarbon molar ratios in the range of 1 to 20, preferably between 4 and 12.

These same catalysts, i.e. those containing hydrogenation promoters, are also useful in hydroisomerization processes in which feedstocks such as normal paraffins are converted to saturated branched chain isomers. Hydroisomerization is carried out at a temperature of from about 200° F. to 600° F. (93° C. to 316° C.), preferably 300° F. to 550° F. (149° C. to 288° C.) with an LHSV value of from about 0.2 to 1.0. Hydrogen (H) is supplied to the reactor in admixture with the hydrocarbon (Hc) feedstock in molar proportions (H/Hc) of between 1 and 5.

At somewhat higher temperatures, i.e. from about 650° F. to 1000° F. (343° C. to 538° C.), preferably 850° F. to 950° F. (454° C. to 510° C.) and usually at somewhat lower pressures within the range of about 15 to 50 p.s.i.g. (205 to 446 KPa.), the same catalyst compositions are used to hydroisomerize normal paraffins. Preferably the paraffin feedstock comprises normal paraffins having a carbon number range of $C_7$-$C_{20}$. Contact time between the feedstock and the catalyst is generally relatively short to avoid undesirable side reactions such as olefin polymerization and paraffin cracking. LHSV values in the range of 0.1 to 10, preferably 1.0 to 6.0 are suitable.

The unique crystal structure of the present BeAPO catalysts and their availability in a form totally void of alkali metal content favor their use in the conversion of alkylaromatic compounds, particularly the catalytic disproportionation of toluene, ethylene, trimethyl benzenes, tetramethyl benzenes and the like. In the disproportionation process, isomerization and transalkylation can also occur. Group VIII noble metal adjuvants alone or in conjunction with Group VI-B metals such as tungsten, molybdenum and chromium are preferably included in the catalyst composition in amounts of from about 3 to 15 weight-% of the overall composition. Extraneous hydrogen can, but need not, be present in the reaction zone which is maintained at a temperature of from about 400° to 750° F. (204° to 399° C.), pressures in the range of 100 to 2000 p.s.i.g. (0.791 to 13.89 MPa.) and LHSV values in the range of 0.1 to 15.

Catalytic cracking processes are preferably carried out with BeAPO compositions using feedstocks such as gas oils, heavy naphthas, deasphalted crude oil residua, etc., with gasoline being the principal desired product. Temperature conditions of 850° to 1100° F. (454° to 593° C.), LHSV values of 0.5 to 10 and pressure conditions of from about 0 to 50 p.s.i.g (101 to 446 KPa.) are suitable.

Dehydrocyclization reactions employing paraffinic hydrocarbon feedstocks, preferably normal paraffins having more than 6 carbon atoms, to form benzene, xylenes, toluene and the like are carried out using essentially the same reaction conditions as for catalytic cracking. For these reactions it is preferred to use the BeAPO catalyst in conjunction with a Group VIII non-noble metal cation such as cobalt and nickel.

In catalytic dealkylation wherein it is desired to cleave paraffinic side chains from aromatic nuclei without substantially hydrogenating the ring structure, relatively high temperatures in the range of about 800°-1000° F. (427°-538° C.) are employed at moderate hydrogen pressures of about 300-1000 p.s.i.g. (2.17-6.895 MPa.), other conditions being similar to those described above for catalytic hydrocracking. Preferred catalysts are of the same type described above in connection with catalytic dehydrocyclization. Particularly desirable dealkylation reactions contemplated herein include the conversion of methylnaphthalene to naphthalene and toluene and/or xylenes to benzene.

In catalytic hydrofining, the primary objective is to promote the selective hydrodecomposition of organic sulfur and/or nitrogen compounds in the feed, without substantially affecting hydrocarbon molecules therein. For this purpose it is preferred to employ the same general conditions described above for catalytic hydrocracking, and catalysts of the same general nature described in connection with dehydrocyclization operations. Feedstocks include gasoline fractions, kerosenes, jet fuel fractions, diesel fractions, light and heavy gas oils deasphalted crude oil residua and the like. Any of these may contain up to about 5 weight-percent of sulfur and up to about 3 weight-percent of nitrogen.

Similar conditions can be employed to effect hydrofining, i.e., denitrogenation and desulfurization, of hydrocarbon feeds containing substantial proportions of organonitrogen and organosulfur compounds. It is generally recognized that the presence of substantial amounts of such constituents markedly inhibits the activity of hydrocracking catalysts Consequently, it is necessary to operate at more extreme conditions when it is desired to obtain the same degree of hydrocracking conversion per pass on a relatively nitrogenous feed than with a feed containing less organonitrogen compounds. Consequently, the conditions under which denitrogenation, desulfurization and/or hydrocracking can be most expeditiously accomplished in any given situation are necessarily determined in view of the characteristics of the feedstocks, in particular the concentration of organonitrogen compounds in the feedstock. As a result of the effect of organonitrogen compounds on the hydrocracking activity of these compositions it is not at all unlikely that the conditions most suitable for denitrogenation of a given feedstock having a relatively high organonitrogen content with minimal hydrocracking, e.g., less than 20 volume percent of fresh feed per pass, might be the same as those preferred for hydrocracking another feedstock having a lower concentration of hydrocracking inhibiting constituents e.g , organonitrogen compounds. Consequently, it has become the practice in this art to establish the conditions under which a certain feed is to be contacted on the basis of preliminary screening tests with the specific catalyst and feedstock.

Isomerization reactions are carried out under conditions similar to those described above for reforming, using somewhat more acidic catalysts. Olefins are preferably isomerized at temperatures of 500°–900° F. (260°–482° C.), while paraffins, naphthenes and alkyl aromatics are isomerized at temperatures of 700°–1000° F. (371°–538° C.). Particularly desirable isomerization reactions contemplated herein include the conversion of n-heptene and/or n-octane to isoheptanes, iso-octanes, butane to iso-butane, methylcyclopentane to cyclohexane, meta-xylene and/or ortho-xylene to paraxylene, 1-butene to 2-butene and/or isobutene, n-hexane to isohexene, cyclohexene to methylcyclopentene etc. The preferred form of the catalyst is a combination of the BeAPO with polyvalent metal compounds (such as sulfides) of metals of Group II-A, Group II-B and rare earth metals. For alkylation and dealkylation processes the BeAPO compositions having pores of at least 5Å are preferred. When employed for dealkylation of alkyl aromatics, the temperature is usually at least 350° F. (177° C.) and ranges up to a temperature at which substantial cracking of the feedstock or conversion products occurs, generally up to about 700° F. (371° C.). The temperature is preferably at least 450° F. (232° C.) and not greater than the critical temperature of the compound undergoing dealkylation. Pressure conditions are applied to retain at least the aromatic feed in the liquid state. For alkylation the temperature can be as low as 250° F. (121° C.) but is preferably at least 350° F. (177° C.). In the alkylation of benzene, toluene and xylene, the preferred alkylating agents are olefins such a ethylene and propylene.

The following examples are provided to further illustrate the use of the BeAPOs of the invention in certain of the processes discussed above, but are not intended to be limitative of the possible uses of the BeAPOs.

EXAMPLE 9

(Cracking tests on BeAPO-5/BeAPO-36)

The n-butane cracking activity of the mixture of BeAPO-5 and BeAPO-36 prepared in Example 1 above was tested in a bench-scale apparatus, in which the reactor was a cylindrical quartz tube 254 mm. in length and 10.3 mm. internal diameter. This reactor was loaded with the as-synthesized mixture of BeAPO-5 and BeAPO-36, which was in the form of particles having sizes of 20–40 U.S. mesh. The mixture was then calcined in situ by heating from ambient temperature to 500° C. under helium, and then holding the sample at 500° C. in air for 1 hour; the weight of the activated mixture in the reactor was 1.1 grams.

A feedstock comprising a helium/n-butane mixture containing 2 mole percent of n-butane was then passed through the reactor at a rate of 50mL/min. The reactor effluent was analyzed after 10 minutes of on-stream operation using conventional gas chromatography techniques. The resultant data showed a pseudo-first-order rate constant ($k_A$) of 3.4. In contrast, commercial amorphous silica-alumina catalysts typically have a rate constant of about 0.14 under the same conditions.

EXAMPLE 10

(Cracking tests on BeAPO-11)

The n-butane cracking activity of the BeAPO-11 prepared in Example 2 above was tested in the same way as in Example 9 above, except that the calcination was effected by heating from ambient temperature to 500° C. under helium and then holding the sample at 600° C. in air for 1 hour, and that the weight of the activated mixture in the reactor was 0.63 gram. The resultant data showed a pseudo-first-order rate constant ($k_A$) of 1.2.

EXAMPLE 11

(Cracking tests on BeAPO-34)

The n-butane cracking activity of the BeAPO-34 prepared in Example 6 above was tested in the same way as in Example 9 above, except that the calcination was effected by heating at 500° C. under a helium flow, and that the weight of the activated mixture in the reactor was 0.94 gram. The resultant data showed a pseudo-first-order rate constant ($k_A$) of 3.7.

EXAMPLE 12

(Cracking tests on BeAPO-20)

The n-butane cracking activity of the BeAPO-20 prepared in Example 8 above was tested in exactly the same way as in Example 9 above, except that the calcination was effected by heating from ambient temperature to 500° C. under helium and then holding the sample at 600° C. in air for 1 hour and that the weight of the activated mixture in the reactor was 0.69 gram. The resultant data showed a pseudo-first-order rate constant ($k_A$) of 0.06.

We claim:

1. Crystalline molecular sieves having three-dimensional microporous framework structures of $BeO_2$, $AlO_2$ and $PO_2$ tetrahedral units having an empirical chemical composition on an anhydrous basis expressed by the formula:

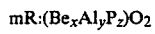

$$mR:(Be_xAl_yP_z)O_2$$

wherein "R" represents at least one organic templating agent present in the intracrystalline pore system; "m" represents the molar amount of "R" present per mole of $(Be_xAl_yP_z)O_2$ and has a value of zero to about 0.3; and "x", "y" and "z" represent the mole fractions of beryllium, aluminum and phosphorus, respectively, present as tetrahedral oxides, said mole fractions being such that they are within the hexagonal compositional area defined by points A, B, C, D, E and F of FIG. 1, said crystalline molecular sieves having a characteristic X-ray powder diffraction pattern which contains at least the d-spacings set forth in one of the following Tables A to H and J to V:

TABLE A

| | (BeAPO-5) | |
|---|---|---|
| 2θ | d(Å) | Relative Intensity |
| 7.3–7.65 | 12.1–11.56 | m–vs |
| 19.5–19.95 | 4.55–4.46 | m–s |
| 20.9–21.3 | 4.25–4.17 | m–vs |
| 22.2–22.6 | 4.00–3.93 | w–vs |
| 25.7–26.15 | 3.47–3.40 | w–m |

TABLE B

| | (BeAPO-11) | |
|---|---|---|
| 2θ | d(Å) | Relative Intensity |
| 9.3–9.65 | 9.51–9.17 | m–s |
| 20.2–20.6 | 4.40–4.31 | m–s |
| 20.9–21.3 | 4.25–4.17 | s–vs |
| 22.0–22.5 | 4.04–3.95 | m–s |
| 22.5–23.0 | 3.95–3.87 | m–s |
| 23.1–23.4 | 3.85–3.80 | m–vs |

TABLE C

| | (BeAPO-14) | |
|---|---|---|
| 2θ | d(Å) | Relative Intensity |
| 8.6–8.9 | 10.3–9.93 | vs |
| 13.0 | 6.81 | w |
| 21.9–22.2 | 4.06–4.00 | w |
| 25.4 | 3.51 | w |
| 27.5 | 3.24 | w |
| 29.7 | 3.01 | w |

TABLE D

| | (BeAPO-16) | |
|---|---|---|
| 2θ | d(Å) | Relative Intensity |
| 11.3–11.6 | 7.83–7.63 | m–vs |
| 18.7–18.9 | 4.75–4.70 | w–s |
| 21.9–22.3 | 4.06–3.99 | m–vs |
| 26.5–27.0 | 3.363–3.302 | w–m |
| 29.7–30.05 | 3.008–2.974 | w–m |

TABLE E

| | (BeAPO-17) | |
|---|---|---|
| 2θ | d(Å) | Relative Intensity |
| 7.7–7.75 | 11.5–11.4 | vs |
| 13.4 | 6.61 | s–vs |
| 15.5–15.55 | 5.72–5.70 | s |
| 19.65–19.7 | 4.52–4.51 | w–s |
| 20.5–20.6 | 4.33–4.31 | vs |
| 31.8–32.00 | 2.812–2.797 | w–s |

TABLE F

| | (BeAPO-18) | |
|---|---|---|
| 2θ | d(Å) | Relative Intensity |
| 9.6–9.65 | 9.21–9.16 | vs |
| 15.5–15.55 | 5.72–5.70 | m |
| 16.9–17.1 | 5.25–5.19 | m |
| 20.15–20.25 | 4.41–4.39 | m |
| 20.95–21.05 | 4.24–4.22 | m |
| 31.8–32.5 | 2.814–2.755 | m |

TABLE G

| | (BeAPO-20) | |
|---|---|---|
| 2θ | d(Å) | Relative Intensity |
| 13.7–14.25 | 6.46–6.22 | m–vs |
| 19.55–20.0 | 4.54–4.44 | w–s |
| 24.05–24.6 | 3.70–3.62 | m–vs |
| 34.3–35.0 | 2.614–2.564 | vw–w |

TABLE G-continued

| | (BeAPO-20) | |
|---|---|---|
| 2θ | d(Å) | Relative Intensity |
| 42.5–43.1 | 2.127–2.098 | vw–w |

TABLE H

| | (BeAPO-31) | |
|---|---|---|
| 2θ | d(Å) | Relative Intensity |
| 8.5–8.6 | 10.40–10.28 | m–s |
| 20.2–20.3 | 4.40–4.37 | m |
| 21.9–22.1 | 4.06–4.02 | w–m |
| 22.6–22.7 | 3.93–3.92 | vs |
| 31.7–31.8 | 2.823–2.814 | w–m |

TABLE J*

| | (BeAPO-33) | |
|---|---|---|
| 2θ | d(Å) | Relative Intensity |
| 9.25–9.55 | 9.56–9.26 | w–m |
| 12.5–12.9 | 7.08–6.86 | vs |
| 16.9–17.3 | 5.25–5.13 | w–m |
| 20.45–20.9 | 4.34–4.25 | w–m |
| 23.85–24.25 | 3.73–3.67 | w–m |
| 26.05–26.35 | 3.42–3.38 | w–m |
| 27.3–27.6 | 3.27–3.23 | vs |

*as-synthesized form

TABLE K*

| | (BeAPO-33) | |
|---|---|---|
| 2θ | d(Å) | Relative Intensity |
| 13.15–13.4 | 6.73–6.61 | vs |
| 18.05–18.35 | 4.91–4.83 | m |
| 18.4–18.6 | 4.82–4.77 | m |
| 26.55–26.7 | 3.36–3.34 | m |
| 32.0–32.1 | 2.80–2.79 | m |

*calcined form

TABLE L

| | (BeAPO-34) | |
|---|---|---|
| 2θ | d(Å) | Relative Intensity |
| 9.4–9.8 | 9.41–9.02 | s–vs |
| 15.9–16.5 | 5.57–5.37 | vw–m |
| 17.85–18.6 | 4.97–4.77 | w–s |
| 20.3–21.3 | 4.37–4.17 | m–vs |
| 24.95–25.4 | 3.57–3.41 | vw–s |
| 30.3–30.8 | 2.95–2.81 | w–s |

TABLE M

| | (BeAPO-35) | |
|---|---|---|
| 2θ | d(Å) | Relative Intensity |
| 10.8–11.1 | 8.19–7.97 | m |
| 17.2–17.4 | 5.16–5.10 | s–vs |
| 21.0–21.25 | 4.23–4.18 | m–s |
| 21.8–22.0 | 4.08–4.04 | vs |
| 31.8–32.2 | 2.814–2.788 | m |

TABLE N

| | (BeAPO-36) | |
|---|---|---|
| 2θ | d(Å) | Relative Intensity |
| 7.7–8.1 | 11.5–10.9 | vs |
| 16.2–16.7 | 5.47–5.3 | w–m |
| 18.9–19.3 | 4.70–4.60 | m–s |
| 20.6–21.1 | 4.31–4.2 | w–s |
| 21.8–22.0 | 4.08–4.04 | m |

TABLE O

| | (BeAPO-37) | |
|---|---|---|
| 2θ | d(Å) | Relative Intensity |
| 6.1–6.3 | 14.49–14.03 | vs |
| 15.5–15.7 | 5.72–5.64 | w–m |
| 18.5–18.8 | 4.80–4.72 | w–m |
| 23.5–23.7 | 3.79–3.75 | w–m |
| 26.9–27.1 | 3.31–3.29 | w–m |

TABLE P

| | (BeAPO-39) | |
|---|---|---|
| 2θ | d(Å) | Relative Intensity |
| 9.4–9.6 | 9.41–9.21 | w–m |
| 13.3–13.6 | 6.66–6.51 | m–vs |
| 18.0–18.4 | 4.93–4.82 | m |
| 21.2–21.5 | 4.19–4.13 | m–s |
| 22.5–23.0 | 3.95–3.87 | s–vs |
| 30.2–30.5 | 2.96–2.93 | w–m |

TABLE Q

| | (BeAPO-40) | |
|---|---|---|
| 2θ | d(Å) | Relative Intensity |
| 7.5–7.7 | 11.79–11.48 | vw–m |
| 8.0–8.1 | 11.05–10.94 | s–vs |
| 12.4–12.5 | 7.14–7.08 | w–vs |
| 13.6–13.8 | 6.51–6.42 | m–s |
| 14.0–14.1 | 6.33–6.28 | w–m |
| 27.8–28.0 | 3.209–3.187 | w–m |

TABLE R

| | (BeAPO-41) | |
|---|---|---|
| 2θ | d(Å) | Relative Intensity |
| 13.6–13.8 | 6.51–6.42 | w–m |
| 20.5–20.6 | 4.33–4.31 | w–m |
| 21.1–21.3 | 4.21–4.17 | vs |
| 22.1–22.3 | 4.02–3.99 | m–s |
| 22.8–23.0 | 3.90–3.86 | m |
| 23.1–23.4 | 3.82–3.80 | w–m |
| 25.5–25.9 | 3.493–3.440 | w–m |

TABLE S

| | (BeAPO-42) | |
|---|---|---|
| 2θ | d(Å) | Relative Intensity |
| 7.15–7.4 | 12.36–11.95 | m–vs |
| 12.5–12.7 | 7.08–6.97 | m–s |
| 21.75–21.9 | 4.09–4.06 | m–s |
| 24.1–24.25 | 3.69–3.67 | vs |
| 27.25–27.4 | 3.273–3.255 | s |
| 30.05–30.25 | 2.974–2.955 | m–s |

TABLE T

| | (BeAPO-44) | |
|---|---|---|
| 2θ | d(Å) | Relative Intensity |
| 9.4–9.55 | 9.41–9.26 | vs |
| 13.0–13.1 | 6.81–6.76 | w–m |
| 16.0–16.2 | 5.54–5.47 | w–m |
| 20.6–20.85 | 4.31–4.26 | s–vs |
| 24.3–24.4 | 3.66–3.65 | w–vs |
| 30.7–30.95 | 2.912–2.889 | w–s |

TABLE U

| | (BeAPO-46) | |
|---|---|---|
| 2θ | d(Å) | Relative Intensity |
| 7.2–8.1 | 12.3–10.9 | vs |
| 21.2–21.8 | 4.19–4.08 | w–m |
| 22.5–23.0 | 3.95–3.87 | vw–m |

TABLE U-continued

| | (BeAPO-46) | |
|---|---|---|
| 2θ | d(Å) | Relative Intensity |
| 26.6–27.2 | 3.351–3.278 | vw–w |
| 28.5–29.0 | 3.132–3.079 | vw–w |

TABLE V

| | (BeAPO-47) | |
|---|---|---|
| 2θ | d(Å) | Relative Intensity |
| 9.4 | 9.41 | vs |
| 15.9–16.0 | 5.57–5.54 | w–m |
| 20.5–20.6 | 4.33–4.31 | s |
| 24.5–24.7 | 3.63–3.60 | w |
| 25.8–25.9 | 3.45–3.44 | w |
| 30.4–30.5 | 2.940–2.931 | w |

2. Crystalline molecular sieves according to claim 1 wherein the mole fractions or beryllium, aluminum and phosphorus present as tetrahedral oxides are within the tetragonal compositional area defined by points a, b, c and d of FIG. 2.

3. Crystalline molecular sieves according to claim 2 wherein the mole fractions of beryllium, aluminum and phosphorus present as tetrahedral oxides are within the triangular compositional area defined by points e, f and g of FIG. 2.

4. Crystalline molecular sieves according to claim 1 wherein "m" is not greater than about 0.15.

5. The crystalline molecular sieves of claim 1 or 2 having a characteristic X-ray powder diffraction pattern which contains at least the d-spacings set forth in Table A given in claim 1.

6. The crystalline molecular sieves of claim 5 wherein the X-ray powder diffraction pattern set forth in Table A contains at least the d-spacings set forth in one of the following Tables AA and AB:

TABLE AA

| | (BeAPO-5) | |
|---|---|---|
| 2θ | d(Å) | Relative Intensity 100 × I/I$_o$ |
| 7.53 | 11.74 | 100 |
| 13.0 | 6.81 | 11 |
| 15.0 | 5.91 | 19 |
| 19.9 | 4.46 | 45 |
| 21.4 | 4.15 | 13 |
| 22.6 | 3.93 | 61 |
| 24.2 | 3.68 | — |
| 26.1 | 3.41 | 30 |
| 29.3 | 3.05 | 9 |
| 30.2 | 2.959 | 19 |
| 34.7 | 2.585 | 14 |
| 38.1 | 2.362 | 3 |
| 47.9 | 1.899 | 5 |

TABLE AB

| | (BeAPO-5) | |
|---|---|---|
| 2θ | d(Å) | Relative Intensity 100 × I/I$_o$ |
| 7.37 | 11.99 | 100 |
| 12.8 | 6.91 | 12 |
| 14.9 | 5.94 | 7 |
| 19.8 | 4.49 | 21 |
| 21.3 | 4.17 | 15 |
| 22.5 | 3.95 | 35 |
| 26.0 | 3.43 | 14 |
| 29.2 | 3.06 | 6 |
| 30.1 | 2.97 | 10 |
| 34.7 | 2.59 | 7 |
| 38.1 | 2.36 | 2 |

TABLE AB-continued (BeAPO-5)

| 2θ | d(Å) | Relative Intensity 100 × I/I$_o$ |
|---|---|---|
| 48.0 | 1.90 | 2 |

7. The crystalline molecular sieves of claim 1 or 2 having a characteristic X-ray powder diffraction pattern which contains at least the d-spacings set forth in Table B given in claim 1.

8. The crystalline molecular sieves of claim 7 wherein the X-ray powder diffraction pattern set forth in Table B contains at least the d-spacings set forth in one of the following Tables BA and BB:

TABLE BA (BeAPO-11)

| 2θ | d(Å) | Relative Intensity 100 × I/I$_o$ |
|---|---|---|
| 8.11 | 10.90 | 43 |
| 9.47 | 9.34 | 58 |
| 13.2 | 6.71 | 21 |
| 15.7 | 5.64 | 38 |
| 16.3 | 5.44 | 6 |
| 19.1 | 4.65 | 6 |
| 20.4 | 4.35 | 56 |
| 21.3 | 4.17 | 100 |
| 22.3 | 3.99 | 58 |
| 22.6 | 3.93 | 54 |
| 22.9 | 3.88 | 65 |
| 23.3 | 3.82 | 86 |
| 24.6 | 3.62 | 7 |
| 24.8 | 3.59 | 8 |
| 25.2 | 3.53 | 6 |
| 26.6 | 3.35 | 38 |
| 28.3 | 3.15 | 6 |
| 28.8 | 3.10 | 19 |
| 29.1 | 3.07 | 6 |
| 29.7 | 3.01 | 8 |
| 31.7 | 2.82 | 10 |
| 32.9 | 2.72 | 22 |
| 34.4 | 2.61 | 11 |
| 36.5 | 2.47 | 6 |
| 38.0 | 2.37 | 9 |
| 39.5 | 2.28 | 4 |
| 43.4 | 2.08 | 4 |
| 44.9 | 2.02 | 7 |
| 50.9 | 1.79 | 6 |

TABLE BB (BeAPO-11)

| 2θ | d(Å) | Relative Intensity 100 × I/I$_o$ |
|---|---|---|
| 8.11 | 10.90 | 50 |
| 9.56 | 9.25 | 50 |
| 13.1 | 6.76 | 24 |
| 15.8 | 5.61 | 50 |
| 20.3 | 4.37 | 32 |
| 21.4 | 4.15 | 100 |
| 22.4 | 3.97 | 69 |
| 23.0 | 3.87 | 52 |
| 23.4 | 3.80 | 56 |
| 24.5 | 3.63 | 4 |
| 25.0 | 3.56 | 5 |
| 26.5 | 3.36 | 19 |
| 26.7 | 3.34 | 14 |
| 29.0 | 3.08 | 16 |
| 29.7 | 3.01 | 9 |
| 31.9 | 2.81 | 10 |
| 32.9 | 2.72 | 15 |
| 34.6 | 2.59 | 5 |
| 36.4 | 2.47 | 7 |
| 38.2 | 2.36 | 9 |
| 43.6 | 2.08 | 3 |

TABLE BB-continued (BeAPO-11)

| 2θ | d(Å) | Relative Intensity 100 × I/I$_o$ |
|---|---|---|
| 45.0 | 2.01 | 4 |

9. The crystalline molecular sieves of claim 1 or 2 having a characteristic X-ray powder diffraction pattern which contains at least the d-spacings set forth in Table C given in claim 1.

10. The crystalline molecular sieves of claim 1 or 2 having a characteristic X-ray powder diffraction pattern which contains at least the d-spacings set forth in Table D given in claim 1.

11. The crystalline molecular sieves of claim 1 or 2 having a characteristic X-ray powder diffraction pattern which contains at least the d-spacings set forth in Table E given in claim 1.

12. The crystalline molecular sieves of claim 1 or 2 having a characteristic X-ray powder diffraction pattern which contains at least the d-spacings set forth in Table F given in claim 1.

13. The crystalline molecular sieves of claim 1 or 2 having a characteristic X-ray powder diffraction pattern which contains at least the d-spacings set forth in Table G given in claim 1.

14. The crystalline molecular sieves of claim 13 wherein the X-ray powder diffraction pattern set forth in Table G contains at least the d-spacings set forth in one of the following Tables GA and GB:

TABLE GA (BeAPO-20)

| 2θ | d(Å) | Relative Intensity 100 × I/I$_o$ |
|---|---|---|
| 14.1 | 6.28 | 63 |
| 20.0 | 4.44 | 45 |
| 22.4 | 3.97 | 11 |
| 24.5 | 3.63 | 100 |
| 28.3 | 3.15 | 17 |
| 31.8 | 2.81 | 11 |
| 34.9 | 2.57 | 16 |
| 40.8 | 2.21 | 3 |
| 43.5 | 2.08 | 5 |
| 48.2 | 1.89 | 4 |
| 52.9 | 1.73 | 5 |

TABLE GB (BeAPO-20)

| 2θ | d(Å) | Relative Intensity 100 × I/I$_o$ |
|---|---|---|
| 14.1 | 6.28 | 100 |
| 20.0 | 4.44 | 42 |
| 22.5 | 3.95 | 12 |
| 24.6 | 3.62 | 97 |
| 28.4 | 3.14 | 16 |
| 31.8 | 2.81 | 14 |
| 35.0 | 2.56 | 15 |
| 40.5 | 2.23 | 3 |
| 43.1 | 2.10 | 5 |
| 48.2 | 1.89 | 3 |
| 52.5 | 1.74 | 8 |

15. The crystalline molecular sieves of claim 1 or 2 having a characteristic X-ray powder diffraction pattern which contains at least the d-spacings set forth in Table H given in claim 1.

16. The crystalline molecular sieves of claim 1 or 2 having a characteristic X-ray powder diffraction pattern which contains at least the d-spacings set forth in Table J given in claim 1.

17. The crystalline molecular sieves of claim 1 or 2 having a characteristic X-ray powder diffraction pattern which contains at least the d-spacings set forth in Table K given in claim 1.

18. The crystalline molecular sieves of claim 1 or 2 having a characteristic X-ray powder diffraction pattern which contains at least the d-spacings set forth in Table L given in claim 1.

19. The crystalline molecular sieves of claim 18 wherein the X-ray powder diffraction pattern set forth in Table L contains at least the d-spacings set forth in one of the following Tables LA, LB and LC:

TABLE LA (BeAPO-34)

| $2\theta$ | d(Å) | Relative Intensity $100 \times I/I_o$ |
|---|---|---|
| 9.74 | 9.08 | 87 |
| 13.1 | 6.76 | 16 |
| 14.4 | 6.15 | 17 |
| 16.3 | 5.44 | 52 |
| 18.4 | 4.82 | 28 |
| 21.0 | 4.23 | 100 |
| 22.7 | 3.92 | 5 |
| 23.5 | 3.79 | 8 |
| 25.7 | 3.47 | 27 |
| 26.3 | 3.39 | 18 |
| 28.1 | 3.18 | 4 |
| 28.9 | 3.09 | 4 |
| 30.1 | 2.97 | 5 |
| 31.1 | 2.88 | 34 |
| 31.8 | 2.81 | 22 |
| 35.0 | 2.56 | 6 |
| 37.0 | 2.43 | 4 |
| 40.4 | 2.23 | 5 |
| 44.2 | 2.05 | 6 |
| 48.4 | 1.88 | 5 |
| 49.8 | 1.83 | 6 |
| 51.9 | 1.76 | 4 |
| 54.0 | 1.70 | 3 |
| 55.5 | 1.66 | 2 |

TABLE LB (BeAPO-34)

| $2\theta$ | d(Å) | Relative Intensity $100 \times I/I_o$ |
|---|---|---|
| 9.78 | 9.04 | 100 |
| 13.2 | 6.71 | 43 |
| 16.4 | 5.41 | 16 |
| 18.4 | 4.82 | 9 |
| 21.2 | 4.19 | 40 |
| 25.7 | 3.47 | 10 |
| 26.7 | 3.34 | 15 |
| 31.5 | 2.84 | 19 |

TABLE LC (BeAPO-34)

| $2\theta$ | d(Å) | Relative Intensity $100 \times I/I_o$ |
|---|---|---|
| 9.80 | 9.03 | 100 |
| 13.2 | 6.71 | 34 |
| 16.5 | 5.37 | 16 |
| 18.6 | 4.77 | 9 |
| 21.3 | 4.17 | 36 |
| 26.1 | 3.41 | 10 |
| 26.7 | 3.34 | 14 |
| 31.6 | 2.83 | 19 |

20. The crystalline molecular sieves of claim 1 or 2 having a characteristic X-ray powder diffraction pattern which contains at least the d-spacings set forth in Table M given in claim 1.

21. The crystalline molecular sieves of claim 1 or 2 having a characteristic X-ray powder diffraction pattern which contains at least the d-spacings set forth in Table N given in claim 1.

22. The crystalline molecular sieves of claim 21 wherein the x-ray powder diffraction pattern set forth in Table N contains at least the d-spacings set forth in the following Table NA:

TABLE NA (BeAPO-36)

| $2\theta$ | d(Å) | Relative Intensity $100 \times I/I_o$ |
|---|---|---|
| 8.04 | 11.00 | 100 |
| 16.7 | 5.31 | 33 |
| 19.3 | 4.60 | — |
| 21.1 | 4.21 | — |
| 22.0 | 4.04 | — |
| 24.2 | 3.68 | — |
| 27.6 | 3.23 | 19 |
| 32.4 | 2.763 | 20 |
| 35.1 | 2.557 | — |

23. The crystalline molecular sieves of claim 1 or 2 having a characteristic X-ray powder diffraction pattern which contains at least the d-spacings set forth in Table O given in claim 1.

24. The crystalline molecular sieves of claim 1 or 2 having a characteristic X-ray powder diffraction pattern which contains at least the d-spacings set forth in Table P given in claim 1.

25. The crystalline molecular sieves of claim 1 or 2 having a characteristic X-ray powder diffraction pattern which contains at least the d-spacings set forth in Table Q given in claim 1.

26. The crystalline molecular sieves of claim 1 or 2 having a characteristic X-ray powder diffraction pattern which contains at least the d-spacings set forth in Table R given in claim 1.

27. The crystalline molecular sieves of claim 1 or 2 having a characteristic X-ray powder diffraction pattern which contains at least the d-spacings set forth in Table S given in claim 1.

28. The crystalline molecular sieves of claim 1 or 2 having a characteristic X-ray powder diffraction pattern which contains at least the d-spacings set forth in Table T given in claim 1.

29. The crystalline molecular sieves of claim 1 or 2 having a characteristic X-ray powder diffraction pattern which contains at least the d-spacings set forth in Table U given in claim 1.

30. The crystalline molecular sieves of claim 1 or 2 having a characteristic X-ray powder diffraction pattern which contains at least the d-spacings set forth in Table V given in claim 1.

31. Process for preparing crystalline molecular sieves having three-dimensional microporous framework structures of $BeO_2$, $Al_2$ and $PO_2$ tetrahedral units having an empirical chemical composition on an anhydrous basis expressed by the formula:

$$mR:(Be_xAl_yP_z)O_2$$

wherein "R" represents at least one organic templating agent present in the intracrystalline pore system; "m" represents the molar amount of "R" present per mole of $(Be_xAl_yP_z)O_2$ and has a value of zero to about 0.3; and "x", "y" and "z" represent the mole fractions of beryllium, aluminum and phosphorus, respectively, present as tetrahedral oxides, said mole fractions being such that they are within the hexagonal compositional area defined by points A, B, C, D, E and F of FIG. 1, said crystalline molecular sieves having a characteristic X-ray powder diffraction pattern which contains at least the d-spacings set forth in one of the following Tables A to H and J to V:

TABLE A (BeAPO-5)

| 2θ | d(Å) | Relative Intensity |
|---|---|---|
| 7.3–7.65 | 12.1–11.56 | m–vs |
| 19.5–19.95 | 4.55–4.46 | m–s |
| 20.9–21.3 | 4.25–4.17 | m–vs |
| 22.2–22.6 | 4.00–3.93 | w–vs |
| 25.7–26.15 | 3.47–3.40 | w–m |

TABLE B (BeAPO-11)

| 2θ | d(Å) | Relative Intensity |
|---|---|---|
| 9.3–9.65 | 9.51–9.17 | m–s |
| 20.2–20.6 | 4.40–4.31 | m–s |
| 20.9–21.3 | 4.25–4.17 | s–vs |
| 22.0–22.5 | 4.04–3.95 | m–s |
| 22.5–23.0 | 3.95–3.87 | m–s |
| 23.1–23.4 | 3.85–3.80 | m–vs |

TABLE C (BeAPO-14)

| 2θ | d(Å) | Relative Intensity |
|---|---|---|
| 8.6–8.9 | 10.3–9.93 | vs |
| 13.0 | 6.81 | w |
| 21.9–22.2 | 4.06–4.00 | w |
| 25.4 | 3.51 | w |
| 27.5 | 3.24 | w |
| 29.7 | 3.01 | w |

TABLE D (BeAPO-16)

| 2θ | d(Å) | Relative Intensity |
|---|---|---|
| 11.3–11.6 | 7.83–7.63 | m–vs |
| 18.7–18.9 | 4.75–4.70 | w–s |
| 21.9–22.3 | 4.06–3.99 | m–vs |
| 26.5–27.0 | 3.363–3.302 | w–m |
| 29.7–30.05 | 3.008–2.974 | w–m |

TABLE E (BeAPO-17)

| 2θ | d(Å) | Relative Intensity |
|---|---|---|
| 7.7–7.75 | 11.5–11.4 | vs |
| 13.4 | 6.61 | s–vs |
| 15.5–15.55 | 5.72–5.70 | s |
| 19.65–19.7 | 4.52–4.51 | w–s |
| 20.5–20.6 | 4.33–4.31 | vs |
| 31.8–32.00 | 2.812–2.797 | w–s |

TABLE F (BeAPO-18)

| 2θ | d(Å) | Relative Intensity |
|---|---|---|
| 9.6–9.65 | 9.21–9.16 | vs |
| 15.5–15.55 | 5.72–5.70 | m |
| 16.9–17.1 | 5.25–5.19 | m |
| 20.15–20.25 | 4.41–4.39 | m |
| 20.95–21.05 | 4.24–4.22 | m |

TABLE F-continued (BeAPO-18)

| 2θ | d(Å) | Relative Intensity |
|---|---|---|
| 31.8–32.5 | 2.814–2.755 | m |

TABLE G (BeAPO-20)

| 2θ | d(Å) | Relative Intensity |
|---|---|---|
| 13.7–14.25 | 6.46–6.22 | m–vs |
| 19.55–20.0 | 4.54–4.44 | w–s |
| 24.05–24.6 | 3.70–3.62 | m–vs |
| 34.3–35.0 | 2.614–2.564 | vw–w |
| 42.5–43.1 | 2.127–2.098 | vw–w |

TABLE H (BeAPO-31)

| 2θ | d(Å) | Relative Intensity |
|---|---|---|
| 8.5–8.6 | 10.40–10.28 | m–s |
| 20.2–20.3 | 4.40–4.37 | m |
| 21.9–22.1 | 4.06–4.02 | w–m |
| 22.6–22.7 | 3.93–3.92 | vs |
| 31.7–31.8 | 2.823–2.814 | w–m |

TABLE J*

(BeAPO-33)

| 2θ | d(Å) | Relative Intensity |
|---|---|---|
| 9.25–9.55 | 9.56–9.26 | w–m |
| 12.5–12.9 | 7.08–6.86 | vs |
| 16.9–17.3 | 5.25–5.13 | w–m |
| 20.45–20.9 | 4.34–4.25 | w–m |
| 23.85–24.25 | 3.73–3.67 | w–m |
| 26.05–26.35 | 3.42–3.38 | w–m |
| 27.3–27.6 | 3.27–3.23 | vs |

*as-synthesized form

TABLE K*

(BeAPO-33)

| 2θ | d(Å) | Relative Intensity |
|---|---|---|
| 13.15–13.4 | 6.73–6.61 | vs |
| 18.05–18.35 | 4.91–4.83 | m |
| 18.4–18.6 | 4.82–4.77 | m |
| 26.55–26.7 | 3.36–3.34 | m |
| 32.0–32.1 | 2.80–2.79 | m |

*calcined form

TABLE L (BeAPO-34)

| 2θ | d(Å) | Relative Intensity |
|---|---|---|
| 9.4–9.8 | 9.41–9.02 | s–vs |
| 15.9–16.5 | 5.57–5.37 | vw–m |
| 17.85–18.6 | 4.97–4.77 | w–s |
| 20.3–21.3 | 4.37–4.17 | m–vs |
| 24.95–25.4 | 3.57–3.41 | vw–s |
| 30.3–30.8 | 2.95–2.81 | w–s |

TABLE M (BeAPO-35)

| 2θ | d(Å) | Relative Intensity |
|---|---|---|
| 10.8–11.1 | 8.19–7.97 | m |
| 17.2–17.4 | 5.16–5.10 | s–vs |
| 21.0–21.25 | 4.23–4.18 | m–s |
| 21.8–22.0 | 4.08–4.04 | vs |
| 31.8–32.2 | 2.814–2.788 | m |

TABLE N

| | (BeAPO-36) | |
|---|---|---|
| 2θ | d(Å) | Relative Intensity |
| 7.7–8.1 | 11.5–10.9 | vs |
| 16.2–16.7 | 5.47–5.3 | w–m |
| 18.9–19.3 | 4.70–4.60 | m–s |
| 20.6–21.1 | 4.31–4.2 | w–s |
| 21.8–22.0 | 4.08–4.04 | m |

TABLE O

| | (BeAPO-37) | |
|---|---|---|
| 2θ | d(Å) | Relative Intensity |
| 6.1–6.3 | 14.49–14.03 | vs |
| 15.5–15.7 | 5.72–5.64 | w–m |
| 18.5–18.8 | 4.80–4.72 | w–m |
| 23.5–23.7 | 3.79–3.75 | w–m |
| 26.9–27.1 | 3.31–3.29 | w–m |

TABLE P

| | (BeAPO-39) | |
|---|---|---|
| 2θ | d(Å) | Relative Intensity |
| 9.4–9.6 | 9.41–9.21 | w–m |
| 13.3–13.6 | 6.66–6.51 | m–vs |
| 18.0–18.4 | 4.93–4.82 | m |
| 21.2–21.5 | 4.19–4.13 | m–s |
| 22.5–23.0 | 3.95–3.87 | s–vs |
| 30.2–30.5 | 2.96–2.93 | w–m |

TABLE Q

| | (BeAPO-40) | |
|---|---|---|
| 2θ | d(Å) | Relative Intensity |
| 7.5–7.7 | 11.79–11.48 | vw–m |
| 8.0–8.1 | 11.05–10.94 | s–vs |
| 12.4–12.5 | 7.14–7.08 | w–vs |
| 13.6–13.8 | 6.51–6.42 | m–s |
| 14.0–14.1 | 6.33–6.28 | w–m |
| 27.8–28.0 | 3.209–3.187 | w–m |

TABLE R

| | (BeAPO-41) | |
|---|---|---|
| 2θ | d(Å) | Relative Intensity |
| 13.6–13.8 | 6.51–6.42 | w–m |
| 20.5–20.6 | 4.33–4.31 | w–m |
| 21.1–21.3 | 4.21–4.17 | vs |
| 22.1–22.3 | 4.02–3.99 | m–s |
| 22.8–23.0 | 3.90–3.86 | m |
| 23.1–23.4 | 3.82–3.80 | w–m |
| 25.5–25.9 | 3.493–3.440 | w–m |

TABLE S

| | (BeAPO-42) | |
|---|---|---|
| 2θ | d(Å) | Relative Intensity |
| 7.15–7.4 | 12.36–11.95 | m–vs |
| 12.5–12.7 | 7.08–6.97 | m–s |
| 21.75–21.9 | 4.09–4.06 | m–s |
| 24.1–24.25 | 3.69–3.67 | vs |
| 27.25–27.4 | 3.273–3.255 | s |
| 30.05–30.25 | 2.974–2.955 | m–s |

TABLE T

| | (BeAPO-44) | |
|---|---|---|
| 2θ | d(Å) | Relative Intensity |
| 9.4–9.55 | 9.41–9.26 | vs |
| 13.0–13.1 | 6.81–6.76 | w–m |
| 16.0–16.2 | 5.54–5.47 | w–m |
| 20.6–20.85 | 4.31–4.26 | s–vs |

TABLE T-continued

| | (BeAPO-44) | |
|---|---|---|
| 2θ | d(Å) | Relative Intensity |
| 24.3–24.4 | 3.66–3.65 | w–vs |
| 30.7–30.95 | 2.912–2.889 | w–s |

TABLE U

| | (BeAPO-46) | |
|---|---|---|
| 2θ | d(Å) | Relative Intensity |
| 7.2–8.1 | 12.3–10.9 | vs |
| 21.2–21.8 | 4.19–4.08 | w–m |
| 22.5–23.0 | 3.95–3.87 | vw–m |
| 26.6–27.2 | 3.351–3.278 | vw–w |
| 28.5–29.0 | 3.132–3.079 | vw–w |

TABLE V

| | (BeAPO-47) | |
|---|---|---|
| 2θ | d(Å) | Relative Intensity |
| 9.4 | 9.41 | vs |
| 15.9–16.0 | 5.57–5.54 | w–m |
| 20.5–20.6 | 4.33–4.31 | s |
| 24.5–24.7 | 3.63–3.60 | w |
| 25.8–25.9 | 3.45–3.44 | w |
| 30.4–30.5 | 2.940–2.931 | w | the process comprising providing a reaction mixture composition at an effective temperature and for an effective time sufficient to produce the molecular sieves, said reaction mixture composition being expressed in terms of molar oxide ratios as follows:

$$aR:(Be_uAl_vP_w)O_2:bH_2O$$

wherein "R" is an organic templating agent; "a" is the amount of "R" and is an effective amount greater than zero to about 6; "b" has a value of from zero to about 500; and "u", "v" and "w" represent the mole fractions, respectively, of beryllium, aluminum and phosphorus in the $(Be_uAl_vP_w)O_2$ constituent, and each has a value of at least 0.01.

32. Process according to claim 31 wherein "x", "y" and "z" are within the pentagonal compositional area defined by points G, H, I, J and K of FIG. 3.

33. Process according to claim 32 wherein "x", "y" and "z" are within the pentagonal compositional area defined by points g, h, i, j and k of FIG. 3.

34. Process according to claim 31 wherein "a" is not greater than about 1.5.

35. Process according to claim 31 wherein "b" has a value of from 2 to 50.

36. Process according to claim 31 wherein the source of phosphorus in the reaction mixture is orthophosphoric acid.

37. Process according to claim 31 wherein the source of phosphorus in the reaction mixture is orthophosphoric acid and the source of aluminum is at least one compound selected from the group consisting of pseudo-boehmite and aluminum alkoxide.

38. Process according to claim 37 wherein the aluminum alkoxide is aluminum isopropoxide.

39. Process according to claim 31 wherein the source of beryllium is selected from the group consisting of oxides, hydroxides, alkoxides, chlorides, bromides, iodides, sulfates, nitrates, carboxylates and mixtures thereof.

40. Process according to claim 31 or claim 32 wherein the organic templating agent is a quaternary ammonium or quaternary phosphonium compound having the formula:

$$R_4X^+$$

wherein X is nitrogen or phosphorus and each R is an alkyl or aryl group containing from 1 to 8 carbon atoms.

41. Process according to claim 31 wherein the organic templating agent is an amine.

42. Process according to claim 31 wherein the templating agent is selected from the group consisting of tetrapropylammonium ion; tetraethylammonium ion; tripropylamine; triethylamine; triethanolamine; piperidine; cyclohexylamine; 2-methyl pyridine; N,N-dimethylbenzylamine; N,N-dimethylethanolamine; choline; N,N-dimethylpiperazine; 1,4-diaziabicyclo-(2,2,2) octane; N-methyldiethanolamine; N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; tetramethylammonium ion; tetrabutylammonium ion; tetrapentylammonium ion; di-n-butylamine; neopentylamine; d-n-pentylamine; isopropylamine; t-butylamine; ethylenediamine; pyrrolidone; 2-imidazolidone; di-n-propylamine; and a polymeric quaternary ammonium salt $[(C_{14}H_{32}N_2)(OH)_2]_x$ wherein x has a value of at least 2.

43. Molecular sieves prepared by calcining, at a temperature sufficiently high to remove at least some of any organic templating agent present in the intracrystalline pore system, the crystalline molecular sieves having three-dimensional microporous framework structures of $BeO_2$, $AlO_2$ and $PO_2$ tetrahedral units having an empirical chemical composition on an anhydrous basis expressed by the formula:

$$mR:(Be_xAl_yP_z)O_2$$

wherein "R" represents at least one organic templating agent present in the intracrystalline pore system; "m" represents the molar amount of "R" present per mole of $(Be_xAl_yP_z)O_2$ and has a value of zero to about 0.3; and "x", "y" and "z" represent the mole fractions of beryllium, aluminum and phosphorus, respectively, present as tetrahedral oxides, said mole fractions being such that they are within the hexagonal compositional area defined by points A, B, C, D, E and F of FIG. 1, said crystalline molecular sieves having a characteristic X-ray powder diffraction pattern which contains at least the d-spacings set forth in one of the following Tables A to H and J to V:

TABLE A

| $2\theta$ | (BeAPO-5) d(Å) | Relative Intensity |
|---|---|---|
| 7.3–7.65 | 12.1–11.56 | m–vs |
| 19.5–19.95 | 4.55–4.46 | m–s |
| 20.9–21.3 | 4.25–4.17 | m–vs |
| 22.2–22.6 | 4.00–3.93 | w–vs |
| 25.7–26.15 | 3.47–3.40 | w–m |

TABLE B

| $2\theta$ | (BeAPO-11) d(Å) | Relative Intensity |
|---|---|---|
| 9.3–9.65 | 9.51–9.17 | m–s |
| 20.2–20.6 | 4.40–4.31 | m–s |
| 20.9–21.3 | 4.25–4.17 | s–vs |
| 22.0–22.5 | 4.04–3.95 | m–s |
| 22.5–23.0 | 3.95–3.87 | m–s |

TABLE B-continued

| $2\theta$ | (BeAPO-11) d(Å) | Relative Intensity |
|---|---|---|
| 23.1–23.4 | 3.85–3.80 | m–vs |

TABLE C

| $2\theta$ | (BeAPO-14) d(Å) | Relative Intensity |
|---|---|---|
| 8.6–8.9 | 10.3–9.93 | vs |
| 13.0 | 6.81 | w |
| 21.9–22.2 | 4.06–4.00 | w |
| 25.4 | 3.51 | w |
| 27.5 | 3.24 | w |
| 29.7 | 3.01 | w |

TABLE D

| $2\theta$ | (BeAPO-16) d(Å) | Relative Intensity |
|---|---|---|
| 11.3–11.6 | 7.83–7.63 | m–vs |
| 18.7–18.9 | 4.75–4.70 | w–s |
| 21.9–22.3 | 4.06–3.99 | m–vs |
| 26.5–27.0 | 3.363–3.302 | w–m |
| 29.7–30.05 | 3.008–2.974 | w–m |

TABLE E

| $2\theta$ | (BeAPO-17) d(Å) | Relative Intensity |
|---|---|---|
| 7.7–7.75 | 11.5–11.4 | vs |
| 13.4 | 6.61 | s–vs |
| 15.5–15.55 | 5.72–5.70 | s |
| 19.65–19.7 | 4.52–4.51 | w–s |
| 20.5–20.6 | 4.33–4.31 | vs |
| 31.8–32.00 | 2.812–2.797 | w–s |

TABLE F

| $2\theta$ | (BeAPO-18) d(Å) | Relative Intensity |
|---|---|---|
| 9.6–9.65 | 9.21–9.16 | vs |
| 15.5–15.55 | 5.72–5.70 | m |
| 16.9–17.1 | 5.25–5.19 | m |
| 20.15–20.25 | 4.41–4.39 | m |
| 20.95–21.05 | 4.24–4.22 | m |
| 31.8–32.5 | 2.814–2.755 | m |

TABLE G

| $2\theta$ | (BeAPO-20) d(Å) | Relative Intensity |
|---|---|---|
| 13.7–14.25 | 6.46–6.22 | m–vs |
| 19.55–20.0 | 4.54–4.44 | w–s |
| 24.05–24.6 | 3.70–3.62 | m–vs |
| 34.3–35.0 | 2.614–2.564 | vw–w |
| 42.5–43.1 | 2.127–2.098 | vw–w |

TABLE H

| $2\theta$ | (BeAPO-31) d(Å) | Relative Intensity |
|---|---|---|
| 8.5–8.6 | 10.40–10.28 | m–s |
| 20.2–20.3 | 4.40–4.37 | m |
| 21.9–22.1 | 4.06–4.02 | w–m |
| 22.6–22.7 | 3.93–3.92 | vs |
| 31.7–31.8 | 2.823–2.814 | w–m |

TABLE J*

| | (BeAPO-33) | |
|---|---|---|
| 2θ | d(Å) | Relative Intensity |
| 9.25–9.55 | 9.56–9.26 | w–m |
| 12.5–12.9 | 7.08–6.86 | vs |
| 16.9–17.3 | 5.25–5.13 | w–m |
| 20.45–20.9 | 4.34–4.25 | w–m |
| 23.85–24.25 | 3.73–3.67 | w–m |
| 26.05–26.35 | 3.42–3.38 | w–m |
| 27.3–27.6 | 3.27–3.23 | vs |

*as-synthesized form

TABLE K*

| | (BeAPO-33) | |
|---|---|---|
| 2θ | d(Å) | Relative Intensity |
| 13.15–13.4 | 6.73–6.61 | vs |
| 18.05–18.35 | 4.91–4.83 | m |
| 18.4–18.6 | 4.82–4.77 | m |
| 26.55–26.7 | 3.36–3.34 | m |
| 32.0–32.1 | 2.80–2.79 | m |

*calcined form

TABLE L

| | (BeAPO-34) | |
|---|---|---|
| 2θ | d(Å) | Relative Intensity |
| 9.4–9.8 | 9.41–9.02 | s–vs |
| 15.9–16.5 | 5.57–5.37 | vw–m |
| 17.85–18.6 | 4.97–4.77 | w–s |
| 20.3–21.3 | 4.37–4.17 | m–vs |
| 24.95–25.4 | 3.57–3.41 | vw–s |
| 30.3–30.8 | 2.95–2.81 | w–s |

TABLE M

| | (BeAPO-35) | |
|---|---|---|
| 2θ | d(Å) | Relative Intensity |
| 10.8–11.1 | 8.19–7.97 | m |
| 17.2–17.4 | 5.16–5.10 | s–vs |
| 21.0–21.25 | 4.23–4.18 | m–s |
| 21.8–22.0 | 4.08–4.04 | vs |
| 31.8–32.2 | 2.814–2.788 | m |

TABLE N

| | (BeAPO-36) | |
|---|---|---|
| 2θ | d(Å) | Relative Intensity |
| 7.7–8.1 | 11.5–10.9 | vs |
| 16.2–16.7 | 5.47–5.3 | w–m |
| 18.9–19.3 | 4.70–4.60 | m–s |
| 20.6–21.1 | 4.31–4.2 | w–s |
| 21.8–22.0 | 4.08–4.04 | m |

TABLE O

| | (BeAPO-37) | |
|---|---|---|
| 2θ | d(Å) | Relative Intensity |
| 6.1–6.3 | 14.49–14.03 | vs |
| 15.5–15.7 | 5.72–5.64 | w–m |
| 18.5–18.8 | 4.80–4.72 | w–m |
| 23.5–23.7 | 3.79–3.75 | w–m |
| 26.9–27.1 | 3.31–3.29 | w–m |

TABLE P

| | (BeAPO-39) | |
|---|---|---|
| 2θ | d(Å) | Relative Intensity |
| 9.4–9.6 | 9.41–9.21 | w–m |
| 13.3–13.6 | 6.66–6.51 | m–vs |
| 18.0–18.4 | 4.93–4.82 | m |
| 21.2–21.5 | 4.19–4.13 | m–s |

TABLE P-continued

| | (BeAPO-39) | |
|---|---|---|
| 2θ | d(Å) | Relative Intensity |
| 22.5–23.0 | 3.95–3.87 | s–vs |
| 30.2–30.5 | 2.96–2.93 | w–m |

TABLE Q

| | (BeAPO-40) | |
|---|---|---|
| 2θ | d(Å) | Relative Intensity |
| 7.5–7.7 | 11.79–11.48 | vw–m |
| 8.0–8.1 | 11.05–10.94 | s–vs |
| 12.4–12.5 | 7.14–7.08 | w–vs |
| 13.6–13.8 | 6.51–6.42 | m–s |
| 14.0–14.1 | 6.33–6.28 | w–m |
| 27.8–28.0 | 3.209–3.187 | w–m |

TABLE R

| | (BeAPO-41) | |
|---|---|---|
| 2θ | d(Å) | Relative Intensity |
| 13.6–13.8 | 6.51–6.42 | w–m |
| 20.5–20.6 | 4.33–4.31 | w–m |
| 21.1–21.3 | 4.21–4.17 | vs |
| 22.1–22.3 | 4.02–3.99 | m–s |
| 22.8–23.0 | 3.90–3.86 | m |
| 23.1–23.4 | 3.82–3.80 | w–m |
| 25.5–25.9 | 3.493–3.440 | w–m |

TABLE S

| | (BeAPO-42) | |
|---|---|---|
| 2θ | d(Å) | Relative Intensity |
| 7.15–7.4 | 12.36–11.95 | m–vs |
| 12.5–12.7 | 7.08–6.97 | m–s |
| 21.75–21.9 | 4.09–4.06 | m–s |
| 24.1–24.25 | 3.69–3.67 | vs |
| 27.25–27.4 | 3.273–3.255 | s |
| 30.05–30.25 | 2.974–2.955 | m–s |

TABLE T

| | (BeAPO-44) | |
|---|---|---|
| 2θ | d(Å) | Relative Intensity |
| 9.4–9.55 | 9.41–9.26 | vs |
| 13.0–13.1 | 6.81–6.76 | w–m |
| 16.0–16.2 | 5.54–5.47 | w–m |
| 20.6–20.85 | 4.31–4.26 | s–vs |
| 24.3–24.4 | 3.66–3.65 | w–vs |
| 30.7–30.95 | 2.912–2.889 | w–s |

TABLE U

| | (BeAPO-46) | |
|---|---|---|
| 2θ | d(Å) | Relative Intensity |
| 7.2–8.1 | 12.3–10.9 | vs |
| 21.2–21.8 | 4.19–4.08 | w–m |
| 22.5–23.0 | 3.95–3.87 | vw–m |
| 26.6–27.2 | 3.351–3.278 | vw–w |
| 28.5–29.0 | 3.132–3.079 | vw–w |

TABLE V

| | (BeAPO-47) | |
|---|---|---|
| 2θ | d(Å) | Relative Intensity |
| 9.4 | 9.41 | vs |
| 15.9–16.0 | 5.57–5.54 | w–m |
| 20.5–20.6 | 4.33–4.31 | s |
| 24.5–24.7 | 3.63–3.60 | w |
| 25.8–25.9 | 3.45–3.44 | w |

TABLE V-continued

| | (BeAPO-47) | |
|---|---|---|
| 2θ | d(Å) | Relative Intensity |
| 30.4–30.5 | 2.940–2.931 | w |

44. Crystalline molecular sieves having three-dimensional microporous framework structures of $BeO_2$, $AlO_2$ and $PO_2$ tetrahedral units having an empirical chemical composition on an anhydrous basis expressed by the formula:

$$mR:(Be_xAl_yP_z)O_2$$

wherein "R" represents at least one organic templating agent present in the intracrystalline pore system; "m" represents the molar amount of "R" present per mole of $(Be_xAl_yP_z)O_2$ and has a value of zero to about 0.3; and "x", "y" and "z" represent the mole fractions of beryllium, aluminum and phosphorus, respectively, present as tetrahedral oxides, said mole fractions being such that they are within the hexagonal compositional area defined by points A, B, C, D, E and F of FIG. 1.

45. Crystalline molecular sieves according to claim 44 wherein the mole fractions of beryllium, aluminum and phosphorus present as tetrahedral oxides are within the tetragonal compositional area defined by points a, b, c and d of FIG. 2.

46. Crystalline molecular sieves according to claim 45 wherein the mole fractions of beryllium, aluminum and phosphorus present as tetrahedral oxides are within the triangular compositional area defined by points e, f and g of FIG. 2.

47. The crystalline molecular sieves according to claim 44 wherein "m" is not greater than about 0.15.

48. Process for preparing crystalline molecular sieves having three-dimensional microporous framework structures of $BeO_2$, $AlO_2$ and $PO_2$ tetrahedral units having an empirical chemical composition on an anhydrous basis expressed by the formula:

$$mR:(Be_xAl_yP_z)O_2$$

wherein "R" represents at least one organic templating agent present in the intracrystalline pore system; "m" represents the molar amount of "R" present per mole of $(Be_xAl_yP_z)O_2$ and has a value of zero to about 0.3; and "x", "y" and "z" represent the mole fractions of beryllium, aluminum and phosphorus, respectively, present as tetrahedral oxides, said mole fractions being such that they are within the hexagonal compositional area defined by points A, B C, D, and E and F of FIG. 1, the process comprising providing a reaction mixture composition at an effective temperature and for an effective time sufficient to produce the molecular sieves, said reaction mixture composition being expressed in terms of molar oxide radios as follows:

$$aR:(Be_uAl_vP_w)O_2: bH_2O$$

wherein "R" is an organic templating agent; "a" is the amount of "R" and is an effective amount greater than zero to about 6; "b" has a value of from zero to about 500; and "u". "v" and "w" represent the mole fractions, respectively, of beryllium, aluminum and phosphorus in the $(Be_uAl_vP_w)O_2$ constituent, and each has a value of at least 0.01.

49. Process according to claim 48 wherein "x", "y" and "z" are within the pentagonal compositional area defined by points G, H, I, J and K of FIG. 3.

50. Process according to claim 49 wherein "x", "y" and "x" are within the pentagonal compositional area defined by points g, h, i, j and k of FIG. 3.

51. Process according to claim 48 wherein "a" is not greater than about 1.5.

52. Process according to claim 48 wherein "b" has a value of from 2 to 50.

53. Process according to claim 48 wherein the source of phosphorus in the reaction mixture is orthophosphoric acid.

54. Process according to claim 48 wherein the source of phosphorus in the reaction mixture is orthophosphoric acid and the source of aluminum is at least one compound selected from the group consisting of pseudo-boehmite and aluminum alkoxide.

55. Process according to claim 54 wherein the aluminum alkoxide is aluminum isopropoxide.

56. Process according to claim 48 wherein the source of beryllium is selected from the group consisting of oxides, hydroxides, alkoxides, chlorides, bromides, iodides, sulfates, nitrates, carboxylates and mixtures thereof.

57. Process according to claim 48 wherein the organic templating agent is a quaternary ammonium or quaternary phosphonium compound having the formula:

$$R_4X^+$$

wherein X is nitrogen or phosphorus and each R is an alkyl or aryl group containing from 1 to 8 carbon atoms.

58. Process according to claim 48 wherein the organic templating agent is an amine.

59. Process according to claim 48 wherein the templating agent is selected from the group consisting of tetrapropylammonium ion; tetraethylammonium ion; tripropylamine; triethylamine; triethanolamine; piperidine; cyclohexylamine; 2-methyl pyridine; N,N-dimethylbenzylamine; N,N-dimethylethanolamine; choline; N,N-dimethylpiperazine; 1,4-diaziabicyclo-(2,2,2) octane; N-methyldiethanolamine; N-methylethanolamine; N-methylpiperidine; 3-methylpiperidine; N-methylcyclohexylamine; 3-methylpyridine; 4-methylpyridine; quinuclidine; N,N,dimethyl-1,4-diazabicyclo (2,2,2) octane ion; tetramethylammonium ion; tetrabutylammonium ion; tetrapentylammonium ion; di-n-butylamine; neopentylamine; di-n-pentylamine; isopropylamine; t-butylamine; ethylenediamine; pyrrolidine; 2-imidazolidone; di-n-propylamine; and a polymeric quaternary ammonium salt $[(C_{14}H_{32}N_2)(OH)_2]_x$ wherein x has a value of at least 2.

60. Molecular sieves prepared by calcining, at a temperature sufficiently high to remove at least some of any organic templating agent present in the intracrystalline pore system, the crystalline molecular sieves having three-dimensional microporous framework structures of $BeO_2$, $AlO_2$ and $PO_2$ tetrahedral units having an empirical chemical composition on an anhydrous basis expressed by the formula:

$$mR:(Be_xAl_yP_z)O_2$$

wherein "R" represents at least one organic templating agent present in the intracrystalline pore system; "m" represents the molar amount of "R" present per mole of $(Be_xAl_yP_z)O_2$ and has a value of zero to about 0.3; and "x", "y" and "z" represent the mole fractions of beryllium, aluminum and phosphorous, respectively, present as tetrahedral oxides, said mole fractions being such that they are within the hexagonal compositional area defined by points A, B, C, D and E and F of FIG. 1

* * * * *